(12) United States Patent  (10) Patent No.: US 7,799,933 B2
Ceccarelli et al.  (45) Date of Patent: *Sep. 21, 2010

(54) SULFONAMIDE DERIVATIVES

(75) Inventors: Simona M. Ceccarelli, Basel (CH); Odile Chomienne, Altkirch (FR); Patrizio Mattei, Riehen (CH); Ulrike Obst Sander, Reinach BL (CH)

(73) Assignee: Hoffman-La Roche Inc., Nutley, NJ (US)

( * ) Notice: Subject to any disclaimer, the term of this patent is extended or adjusted under 35 U.S.C. 154(b) by 105 days.

This patent is subject to a terminal disclaimer.

(21) Appl. No.: 11/951,426

(22) Filed: Dec. 6, 2007

(65) Prior Publication Data

US 2008/0153805 A1 Jun. 26, 2008

(30) Foreign Application Priority Data

Dec. 21, 2006 (EP) .................................. 06126920

(51) Int. Cl.
*A61K 31/404* (2006.01)
*C07D 209/12* (2006.01)

(52) U.S. Cl. .................. 548/510; 548/127; 548/128; 548/195; 548/200; 548/364.7; 548/467; 548/491; 548/503; 514/415; 514/371; 514/407

(58) Field of Classification Search .................. 548/469, 548/490, 491, 127, 128, 195, 200, 364.7, 548/467, 503, 510; 514/415, 419, 371, 407
See application file for complete search history.

(56) References Cited

U.S. PATENT DOCUMENTS

2007/0060567 A1* 3/2007 Ackermann et al. .... 514/217.01

FOREIGN PATENT DOCUMENTS

WO   WO 01/21577      3/2001
WO   WO 2006/131452  12/2006
WO   WO 2007/031429   3/2007

OTHER PUBLICATIONS

Giannessi et. al. "Reversible Carnitine Palmitoyltransferase Inhibitors with Broad Chemical Diversity as Potential Antidiabetic Agents." Journal of Medicinal Chemistry, 2001, 44(15), 2383-2386.*
Hulme, C et al, *Bioorganic & Med. Chem. Letters*, vol. 8(14) (1998) 1867-1872.

* cited by examiner

*Primary Examiner*—Rita J Desai
*Assistant Examiner*—David K O'Dell
(74) *Attorney, Agent, or Firm*—George W. Johnston; Dennis P. Tramaloni; Brian C. Remy

(57) ABSTRACT

The invention is concerned with novel sulfonamide derivatives of formula (I)

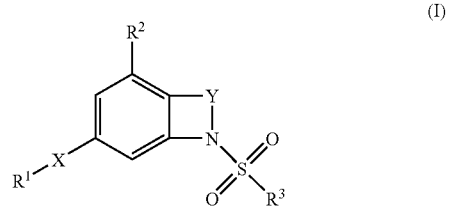

(I)

wherein $R^1$, $R^2$, $R^3$, X and Y are as defined in the description and in the claims, as well as physiologically acceptable salts and esters thereof. These compounds inhibit L-CPT1 and can be used as medicaments.

19 Claims, No Drawings

SULFONAMIDE DERIVATIVES

PRIORITY OF RELATED APPLICATION(S)

This application claims the benefit of European Patent Application No. 06126920.5, filed Dec. 21, 2006, which is hereby incorporated by reference in its entirety.

BACKGROUND OF THE INVENTION

High levels of free fatty acids (FFA) lead to an increase of liver mitochondrial β-oxidation, which is crucial to drive efficient gluconeogenesis. The mitochondrial oxidation of long-chain FFA requires the intervention of two membrane-bound carnitine-dependent palmitoyltransferases (CPTs). CPT1, the outer mitochondrial membrane enzyme, catalyzes the formation of long-chain acylcarnitines. Liver (L-CPT1) and muscle (M-CPT1) CPT1 isoforms are encoded by two different genes and inhibited by malonyl-CoA. The N-ter domain of L-CPT1 confers its lower sensitivity to malonyl CoA. CPT2, the inner mitochondrial membrane enzyme, reconverts long-chain acylcarnitines into long-chain acyl CoA esters. Long-chain acyl-CoAs are then β-oxidized to acetyl-CoA, which activates the pyruvate carboxylase and gluconeogenesis. According to the mechanism of action described above, pharmaceutically active substances which inhibit L-CPT1 reduce liver β-oxidation, consequently inhibit gluconeogenesis and therefore counteract hyperglycemia.

SUMMARY OF THE INVENTION

In sum, the present invention relates to the compounds of formula (I):

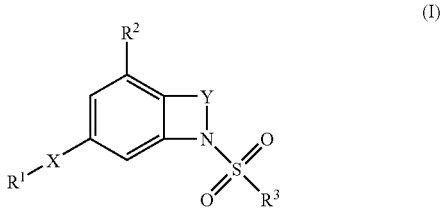

or a pharmaceutically acceptable salt or ester thereof wherein $R^1$-$R^3$, X and Y are as defined in the detailed description and in the claims. The compounds of formula I inhibit liver carnitine palmitoyl transferase 1 (L-CPT1) activity.

The compounds of the present invention can be used as pharmaceutically active agents which are useful in the prevention and/or treatment of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus (also referred to as diabetes type II), obesity, hypertension, insulin resistance syndrome, metabolic syndrome, hyperlipidemia, hypercholesterolemia, fatty liver disease) atherosclerosis, congestive heart failure and renal failure.

Further, the invention is concerned with a process for the manufacture of the above compounds, pharmaceutical preparations which contain such compounds as well as the use of these compounds for the production of pharmaceutical preparations.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven carbon atoms. In preferred embodiments, a lower group has one to four carbon atom(s).

The term "halogen" refers to fluorine, chlorine, bromine or iodine. In preferred embodiments, the halogen is fluorine, chlorine or bromine.

The term "alkyl", alone or in combination with other groups, refers to a branched or straight-chain monovalent saturated aliphatic hydrocarbon radical of one to twenty carbon atoms. In preferred embodiments, the alkyl has one to sixteen carbon atoms, and more preferably one to ten carbon atoms. Lower-alkyl groups as described below also are preferred alkyl groups. Alkyl groups can optionally be substituted with hydroxy, lower-alkoxy, $NH_2$, $N(H,lower-alkyl)$ or $N(lower-alkyl)_2$. Unless specifically stated otherwise, unsubstituted alkyl groups are preferred.

The term "lower-alkyl", alone or in combination with other groups, refers to a branched or straight-chain monovalent alkyl radical of one to seven carbon atoms. In preferred embodiments, the lower alkyl has one to four carbon atoms. This term is further exemplified by such radicals as methyl, ethyl, n-propyl, isopropyl, n-butyl, s-butyl, t-butyl and the like. Lower-alkyl groups can optionally be substituted with hydroxy, lower-alkoxy, $NH_2$, $N(H,lower-alkyl)$ or $N(lower-alkyl)_2$. Unless specifically stated otherwise, unsubstituted lower-alkyl groups are preferred.

The term "cycloalkyl" refers to a monovalent carbocyclic radical of 3 to 10 carbon atoms. In preferred embodiments, the cycloalkyl has 3 to 6 carbon atoms, such as cyclopropyl, cyclobutyl, cyclopentyl, or cyclohexyl.

The term "fluoro-lower-alkyl" refers to lower-alkyl groups which are mono- or multiply substituted with fluorine. Examples of fluoro-lower-alkyl groups include $CFH_2$, $CF_2H$, $CF_3$, $CF_3CH_2$, $CF_3(CH_2)_2$, $(CF_3)_2CH$ and $CF_2H-CF_2$.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups include $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "acid isostere" refers to groups which have similar steric and electronic features of a carboxylic acid, or that are known in the art to mimic the spatial arrangement and electronic properties of a carboxylic acid. Examples of acid isosteres are 1H-tetrazol-5-yl, 4H-[1,2,4]oxadiazol-3-yl-5-one, 4H-[1,2,4]thiadiazol-3-yl-5-one, 4H-[1,2,4]oxadiazol-3-yl-5-thione, 3H-[1,2,3,5]oxathiadiazol-4-yl-2-oxide, $SO_3H$, 3-hydroxy-isooxazol, 3-hydroxy-pyran-4-one or $P(O)(OCH_2CH_3)OH$.

The term "aryl", alone or in combination, relates to the phenyl or naphthyl group, preferably the phenyl group, which can optionally be substituted, unless specifically stated otherwise, by 1 to 5 substituents, independently selected from the group consisting of halogen, hydroxy, amino, $NO_2$, lower-alkyl, hydroxy-lower-alkyl, lower-alkoxy, carboxy, carboxy-lower-alkyl, $H_2NC(O)$, $(H,lower-alkyl)NC(O)$, $(lower-alkyl)_2 NC(O)$, fluoro-lower-alkyl, lower-alkyl-$SO_2$, lower-alkyl-$SO_2O$, lower-alkyl-$SO_2$—NH, lower-alkyl-$SO_2$—N(lower-alkyl), $H_2NSO_2$, $(H,lower-alkyl)NSO_2$, $(lower-alkyl)_2 NSO_2$, cyano, heteroaryl, cycloalkyl, phenyl and phenyloxy. In preferred embodiments the aryl is a pheny group and the number of substituents ranges from 1 to 3. Preferred substituents are halogen, lower-alkyl and lower-alkoxy. Furthermore, aryl groups can preferably be substituted as described in the description and claims below.

The term "heteroaryl" refers to an aromatic 5 to 6 membered monocyclic ring or 9 to 10 membered bicyclic ring which can comprise 1, 2 or 3 atoms of nitrogen, oxygen or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzoisothiazolyl, benzoxazolyl, benzoisoxazolyl and quinolinyl. Preferred heteroaryl groups are thiazolyl, pyrazolyl and thiadiazolyl. Unless specifically stated otherwise, a heteroaryl group may optionally have a substitution pattern as described earlier in connection with the term "aryl". Furthermore, heteroaryl groups can preferably be substituted as described in the description below.

Compounds of formula (I) can form pharmaceutically acceptable salts with physiologically compatible bases. Examples of such salts are alkaline, earth-alkaline and ammonium salts such as sodium, potassium, calcium and trimethylammonium salts.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In reference to a particular group or molecule, the term "substituted" refers to the fact that at least one of the hydrogen atoms of that group or molecule is replaced by some other substituent.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 300 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" means any compound selected from the genus of compounds as defined by the formula.

In detail, the present invention relates to the compounds of formula (I):

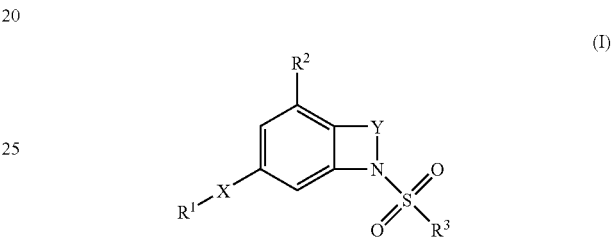

wherein:
X is —NHC(O)— or —C(O)NH—;
Y is selected from the group consisting of:
(a) —C(R$^4$R$^5$)—,
(b) —C(R$^4$R$^5$)C(R$^6$R$^7$)—,
(c) —C(R$^4$R$^5$)C(R$^6$R$^7$)C(R$^8$R$^9$)—,
(d) —C(R$^4$R$^5$)C(R$^6$R$^7$)C(R$^8$R$^9$)C(R$^{10}$R$^{11}$)—, and
(e) —CR$^4$=CR$^6$—;

R$^1$ is aryl or heteroaryl, which aryl or heteroaryl is substituted with —C(R$^{12}$R$^{13}$)[C(R$^{14}$R$^{15}$)]$_n$C(O)OR$^{16}$, and which aryl or heteroaryl in addition is optionally substituted with 1 to 2 substituents independently selected from the group consisting of lower-alkyl, hydroxy, halogen, lower-alkoxy, fluoro-lower-alkyl and fluoro-lower-alkoxy;

R$^2$ is hydrogen, lower-alkyl, hydroxy, halogen, lower-alkoxy, fluoro-lower-alkyl, or fluoro-lower-alkoxy;

R$^3$ is aryl which is optionally substituted with 1 to 3 substituents independently selected from the group consisting of halogen, cyano, hydroxy, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H,lower-alkyl)-S(O)$_2$, N(lower-alkyl)$_2$-S(O)$_2$, NH$_2$—C(O), N(H, lower-alkyl)-C(O), N(lower-alkyl)$_2$-C(O) and lower-alkoxy-C(O), wherein lower-alkyl is optionally substituted with hydroxy, lower-alkoxy, NH$_2$, N(H,lower-alkyl), or N(lower-alkyl)$_2$;

R$^4$, R$^5$, R$^6$, R$^7$, R$^8$, R$^9$, R$^{10}$ and R$^{11}$ independently from each other are selected from the group consisting of hydrogen, halogen, lower-alkyl, lower-alkoxy, fluoro-lower-alkyl, fluoro-lower-alkoxy, hydroxyl, and hydroxy-lower-alkyl;

R$^{12}$, R$^{13}$, R$^{14}$ and R$^{15}$ independently from each other are selected from the group consisting of hydrogen, halogen, lower-alkyl, lower-alkoxy, fluoro-lower-alkyl, fluoro-lower-alkoxy, hydroxy, and hydroxy-lower-alkyl; or alternatively R$^{13}$ is H and R$^{12}$ is —(CH$_2$)$_{1-3}$— and forms a bridge to the aryl or heteroaryl, to which the —C($R^{12}R^{13}$)[C($R^{14}R^{15}$)]$_n$C(O)O$R^{16}$ is bound;

$R^{16}$ is hydrogen or lower-alkyl; and n is 0 or 1.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, mixture of stereoisomers or as optically pure compounds.

A preferred embodiment of the present invention relates to compounds of formula (I) as described above, wherein X is —NH—C(O)—. In such compounds, the left side of X, i.e. the nitrogen atom, is bound to $R^1$.

Other preferred compounds of the present invention are those, wherein Y is —C($R^4R^5$)C($R^6R^7$)—, —C($R^4R^5$)C($R^6R^7$)C($R^8R^9$)—, —C($R^4R^5$)C($R^6R^7$)C($R^8R^9$)C($R^{10}R^{11}$)— or —C$R^4$=C$R^6$—, and $R^4$, $R^5$, $R^6$, $R^7$, $R^8$, $R^9$, $R^{10}$ and $R^{11}$ are as defined for Y is —C($R^4R^5$)C($R^6R^7$)— or —C($R^4R^5$)C($R^6R^7$)C($R^8R^9$)—, and $R^4$, $R^5$, $R^6$, $R^7$, $R^8$ and $R^9$ are as defined for formula (I). All of the above mentioned options for Y also individually constitute separate preferred embodiments.

Another preferred embodiment of the present invention refers to compounds as defined above, wherein $R^1$ is aryl or a heteroaryl selected from the group consisting of thiazolyl, pyrazolyl and thiadiazolyl, which aryl or heteroaryl is substituted with —C($R^{12}R^{13}$)[C($R^{14}R^{15}$)]$_n$C(O)O$R^{16}$, and which aryl or heteroaryl in addition is optionally substituted with lower-alkyl, wherein $R^{12}$, $R^{13}$, $R^{14}$, $R^{15}$, $R^{16}$ and n are as defined for formula (I). More preferably, $R^1$ is phenyl or a heteroaryl selected from the group consisting of thiazolyl and pyrazolyl, which aryl or heteroaryl is substituted with —C($R^{12}R^{13}$)[C($R^{14}R^{15}$)]$_n$C(O)O$R^{16}$, wherein $R^{12}$, $R^{13}$, $R^{14}$, $R^{15}$, $R^{16}$ and n are as defined for formula (I). Even more preferably, $R^1$ is 4-carboxymethyl-phenyl, 4-carboxymethyl-thiazol-2-yl or 1-carboxymethyl-pyrazol-3-yl.

Other preferred compounds of the present invention are those, wherein $R^2$ is hydrogen or lower-alkyl, more preferably wherein $R^2$ is hydrogen or methyl.

Furthermore, compounds as defined above are preferred, wherein $R^3$ is aryl which is optionally substituted with 1 to 3 substituents independently selected form the group consisting of halogen, lower-alkyl and lower-alkoxy. More preferably, $R^3$ is 3,5-dimethyl-phenyl, 3-chloro-phenyl, 2-methoxy-5-chloro-phenyl or 2-methoxy-5-methyl-phenyl.

Still other preferred compounds are those, wherein $R^4$, $R^5$, $R^6$, $R^7$, $R^8$, $R^9$, $R^{10}$ and $R^{11}$ are hydrogen. It is furthermore preferred, that $R^{12}$, $R^{13}$, $R^{14}$ and $R^{15}$ independently from each other are hydrogen, lower-alkyl or hydroxy; or $R^{13}$ is H and $R^{12}$ is —(CH$_2$)$_{2-3}$— and forms a bridge to the aryl or heteroaryl, to which the —C($R^{12}R^{13}$)[C($R^{14}R^{15}$)]$_n$C(O)O$R^{16}$ is bound. In case $R^{12}$ forms a bridge to the aryl or heteroaryl, $R^{12}$ is preferably bound to the ring atom of the aryl or heteroaryl adjacent to the ring atom to which the —C($R^{12}R^{13}$)[C($R^{14}R^{15}$)]$_n$C(O)O$R^{16}$ is bound.

Preferably, $R^{12}$ is hydrogen. Preferably, $R^{13}$ is hydrogen. Preferably, $R^{14}$ and $R^{15}$ are hydrogen. Furthermore, it is preferred that $R^{16}$ is hydrogen. Other preferred compounds are those, wherein n is 0.

In particular, preferred compounds are the compounds of formula (I) described in the examples as individual compounds as well as pharmaceutically acceptable salts as well as pharmaceutically acceptable esters thereof. Furthermore, the substituents as found in the specific examples described below, individually constitute separate preferred embodiments of the present invention.

Preferred compounds of formula (I) are those selected from the group consisting of:

(4-{[1-(5-Chloro-2-methoxy-benzenesulfonyl)-1H-indole-6-carbonyl]-amino}-phenyl)-acetic acid, (4-{[1-(2-Methoxy-5-methyl-benzenesulfonyl)-1H-indole-6-carbonyl]-amino}-phenyl)-acetic acid, (4-{[1-(3,5-Dimethyl-benzenesulfonyl)-1H-indole-6-carbonyl]-amino}-phenyl)-acetic acid, (4-{[1-(3-Chloro-benzenesulfonyl)-1H-indole-6-carbonyl]-amino}-phenyl)-acetic acid, (4-{[1-(2-Methoxy-5-methyl-benzenesulfonyl)-2,3-dihydro-1H-indole-6-carbonyl]-amino}-phenyl)-acetic acid, (4-{[1-(3,5-Dimethyl-benzenesulfonyl)-2,3-dihydro-1H-indole-6-carbonyl]-amino}-phenyl)-acetic acid, (4-{[1-(3-Chloro-benzenesulfonyl)-2,3-dihydro-1H-indole-6-carbonyl]-amino}-phenyl)-acetic acid, (2-{[1-(3,5-Dimethyl-benzenesulfonyl)-2,3-dihydro-1H-indole-6-carbonyl]-amino}-thiazol-4-yl)-acetic acid, (2-{[1-(3-Chloro-benzenesulfonyl)-2,3-dihydro-1H-indole-6-carbonyl]-amino}-thiazol-4-yl)-acetic acid, (4-{[1-(5-Chloro-2-methoxy-benzenesulfonyl)-2,3-dihydro-1H-indole-6-carbonyl]-amino}-phenyl)-acetic acid, (2-{[1-(5-Chloro-2-methoxy-benzenesulfonyl)-2,3-dihydro-1H-indole-6-carbonyl]-amino}-thiazol-4-yl)-acetic acid, (2-{[1-(5-Chloro-2-methoxy-benzenesulfonyl)-2,3-dihydro-1H-indole-6-carbonyl]-amino}-5-methyl-thiazol-4-yl)-acetic acid, (3-{[1-(5-Chloro-2-methoxy-benzenesulfonyl)-2,3-dihydro-1H-indole-6-carbonyl]-amino}-pyrazol-1-yl)-acetic acid, (4-{[1-(5-Chloro-2-methoxy-benzenesulfonyl)-4-methyl-2,3-dihydro-1H-indole-6-carbonyl]-amino}-phenyl)-acetic acid, (2-{[1-(5-Chloro-2-methoxy-benzenesulfonyl)-4-methyl-2,3-dihydro-1H-indole-6-carbonyl]-amino}-thiazol-4-yl)-acetic acid, (2-{[1-(5-Chloro-2-methoxy-benzenesulfonyl)-2,3,4,5-tetrahydro-1H-benzo[b]azepine-8-carbonyl]-amino}-thiazol-4-yl)-acetic acid, (4-{[1-(2-Methoxy-5-methyl-benzenesulfonyl)-1,2,3,4-tetrahydro-quinoline-7-carbonyl]-amino}-phenyl)-acetic acid, (5-{[1-(2-Methoxy-5-methyl-benzenesulfonyl)-1,2,3,4-tetrahydro-quinoline-7-carbonyl]-amino}-[1,2,4]thiadiazol-3-yl)-acetic acid, Hydroxy-(4-{[1-(2-methoxy-5-methyl-benzenesulfonyl)-1,2,3,4-tetrahydro-quinoline-7-carbonyl]-amino}-phenyl)-acetic acid, 2-{1-(2-Methoxy-5-methyl-benzenesulfonyl)-1,2,3,4-tetrahydro-quinoline-7-carbonyl]-amino}-5,6-dihydro-4H-cyclopentathiazole-4-carboxylic acid, (2-{[1-(2-Methoxy-5-methyl-benzenesulfonyl)-1,2,3,4-tetrahydro-quinoline-7-carbonyl]-amino}-thiazol-4-yl)-acetic acid, 2-(4-{[1-(2-Methoxy-5-methyl-benzenesulfonyl)-1,2,3,4-tetrahydro-quinoline-7-carbonyl]-amino}-phenyl)-propionic acid, 2-{1-(2-Methoxy-5-methyl-benzenesulfonyl)-1,2,3,4-tetrahydro-quinoline-7-carbonyl]-amino}-4,5,6,7-tetrahydro-benzothiazole-4-carboxylic acid, and {4-[1-(5-Chloro-2-methoxy-benzenesulfonyl)-1,2,3,4-tetrahydro-quinolin-7-ylcarbamoyl]-phenyl}-acetic acid, and pharmaceutically acceptable salts and esters thereof.

Particularly preferred compounds of formula (I) are those selected from the group consisting of:

(2-{[1-(3,5-Dimethyl-benzenesulfonyl)-2,3-dihydro-1H-indole-6-carbonyl]-amino}-thiazol-4-yl)-acetic acid, (2-{[1-(3-Chloro-benzenesulfonyl)-2,3-dihydro-1H-indole-6-carbonyl]-amino}-4-yl)-acetic acid, (4-{[1-(5-Chloro-2-methoxy-benzenesulfonyl)-2,3-dihydro-1H-indole-6-carbonyl]-amino}-phenyl)-acetic acid, (2-{[1-(5-Chloro-2-methoxy-benzenesulfonyl)-2,3-dihydro-1H-indole-6-carbonyl]-amino}-thiazol-4-yl)-acetic acid (3-{[1-(5-Chloro-2-methoxy-benzenesulfonyl)-2,3-dihydro-1H-indole-6-carbonyl]-amino}-pyrazol-1-yl)-acetic acid, (4-{[1-(5-Chloro-2-methoxy-benzenesulfonyl)-4-methyl-2,3-dihydro-1H-indole-6-carbonyl]-amino}-phenyl)-acetic acid, (2-{[1-(5-Chloro-2-methoxy-benzenesulfonyl)-4-methyl-2,3-dihydro-1H-indole-6-carbonyl]-amino}-thiazol-4-yl)-acetic acid (4-{[1-(2-Methoxy-5-methyl-benzenesulfonyl)-1,2,3,4-tetrahydro-quinoline-7-carbonyl]-amino}-phenyl)-acetic acid (2-{[1-(2-Methoxy-5-methyl-benzenesulfonyl)-1,2,3,4-tetrahydro-quinoline-7-carbonyl]-amino}-thiazol-4-yl)-acetic acid and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises reacting a compound of formula (VI)

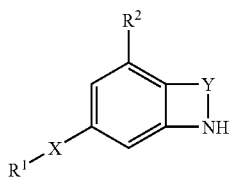

(VI)

with a compound of formula Cl—SO$_2$—R$^3$, wherein R$^1$, R$^2$, R$^3$, X and Y are as defined for formula (I).

The reaction of a compound of formula (VI) with a compound of formula Cl—SO$_2$—R$^3$ can be carried out under conditions well known to the person skilled in the art. For example, the compound of formula (VI) is reacted with a compound of formula Cl—SO$_2$—R$^3$ in anhydrous solvents such as dichloromethane, tetrahydrofuran, acetonitrile, toluene and mixtures thereof or in the absence of solvent, at temperatures between 0° C. and 110° C., optionally in the presence of a base like triethylamine, diisopropylethylamine or pyridine.

The present invention also relates to compounds of formula (I) as defined above, when prepared by a process as described above.

The compounds of formula (VI) and Cl—SO$_2$—R$^3$ can be prepared by methods known in the art or as described below or in analogy thereto. Unless otherwise indicated, R$^1$, R$^2$, R$^3$, X and Y are as described above.

Compounds of formula I where Y is —CR$^4$═CR$^6$— and X is —NHC(O)— are part of the present invention and are represented by general formula II

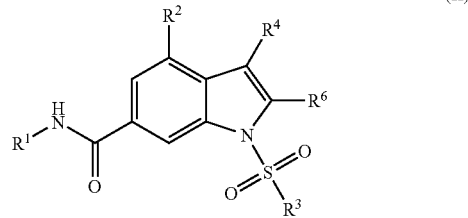

(II)

Compounds of general formula II can be accessed according to general scheme 1:

Scheme 1

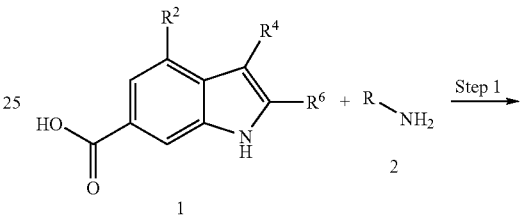

1

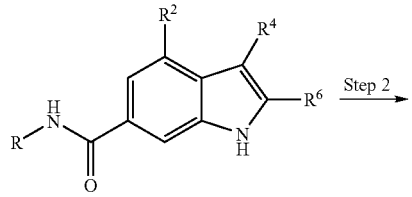

3

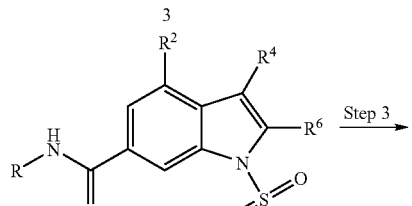

4

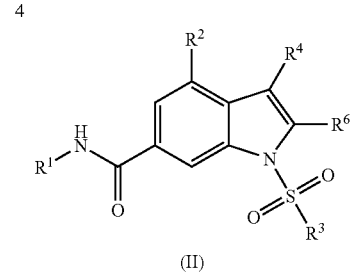

(II)

In step 1, scheme 1, indole-6-carboxylic acids of general formula 1 are coupled to a suitably protected amine derivative 2 according to methods well known to somebody skilled in the art, e.g. amide formation using a coupling reagent. The reaction is typically carried out in aprotic solvents such as dichloromethane, tetrahydrofuran, N,N-dimethylformamide, N-methylpyrrolidinone and mixtures thereof at temperatures between 0° C. and 60° C. in the presence or absence of a base such as triethylamine, diisopropylethylamine or 4-(dimethylamino)-pyridine. Typically used coupling agents are N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate and bromo-tris-pyrrolidino-phosphonium hexafluorophosphate. In step 2, scheme 1, the obtained indole-6-carboxylic acid amides 3 are converted to the sulfonamide derivatives 4 according to methods well known in the art, e.g. sulfonylation of the indole NH. The reaction is typically carried with sulfonyl chlorides as sulfonylation agents in the presence of an organic or inorganic base, like for example potassium tert-butylate, sodium hydride, sodium carbonate, sodium hydroxide or the like. In cases where an inorganic base is used, phase transfer conditions can be applied with a suitable phase transfer catalyst, like for example tetrabutylammonium hydrogensulfate, tetrabutylammonium hydroxide and tetrabutylammonium bromide. In step 3, scheme 1, the protected carboxylic acid embedded in the R group of structure 4 is deprotected to yield the final compounds of general formula (II). Deprotection conditions are chosen based on the nature of the protecting group and can involve simple hydrolysis in aqueous basic conditions, according to methods well known in the art, acidic hydrolysis with aqueous mineral acids, acidic deprotection with mineral acids in non-aqueous solvents, or other deprotection methods based on the state of the art and the nature of the protecting group.

Compounds of general formula I where Y is —C(R⁴R⁵)C(R⁶R⁷)—, R⁵ and R⁷ are hydrogen and X is —NHC(O)— are part of the present invention and are represented by general formula III

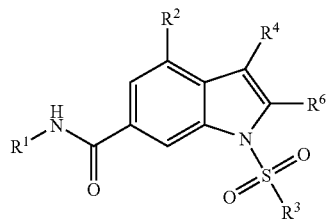

(III)

Compounds of general formula (III) can be accessed according to the method outlined in scheme 2:

Scheme 2

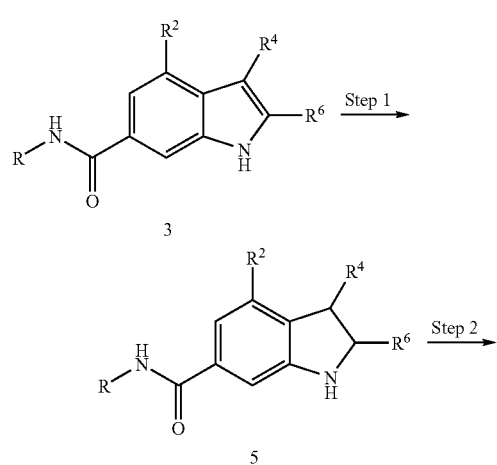

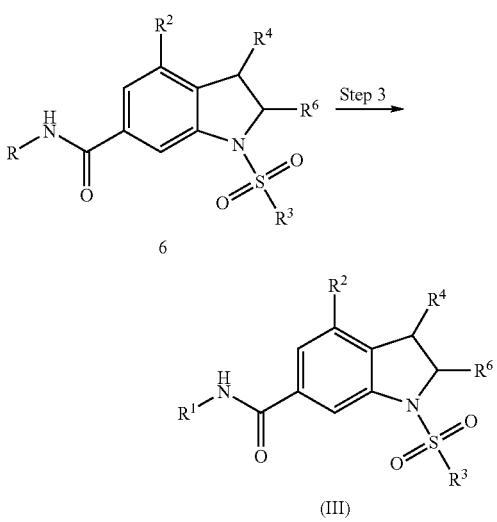

In step 1, scheme 2, compounds of general formula 3 are reduced to the corresponding indolines of general formula 5 according to methods well known to somebody skilled in the art, e.g. partial indole reduction. The reaction is typically carried out in protic solvents such as acetic acid, trifluoroacetic acid, and mixtures thereof at temperatures between 0° C. and 30° C. Typically used reducing reagents are sodium cyanoborohydride, sodium triacetoxyborohydride and sodium borohydride. In step 3, scheme 2, the obtained compounds of general formula 5 are converted into their corresponding sulphonamides of general formula 6, using methods well known to someone skilled in the art, e.g. sulphonylation of amines with sulphonyl chlorides. The reaction is typically carried out in anhydrous solvents such as dichloromethane, tetrahydrofuran, acetonitrile, toluene and mixtures thereof, or in the absence of a solvent, at temperatures between 0° C. and 110° C., optionally in the presence of a base like triethylamine, diisopropylethylamine or pyridine. In step 3, scheme 2, the protected carboxylic acid embedded in the group R of structure 6 is deprotected to yield the final compounds of general formula (III), in analogy to what described for scheme 1, step 3.

Compounds of general formula (I) where Y is —C(R⁴R⁵)C(R⁶R⁷)—, —(R⁴R⁵)C(R⁶R⁷)C(R⁸R⁹)— or —C(R⁴R⁵)C(R⁶R⁷)C(R⁸R⁹)C(R¹⁰R¹¹)— and X is —NHC(O)— are part of the present invention and can be represented by the general formula (IV), where Y' is Y as defined above:

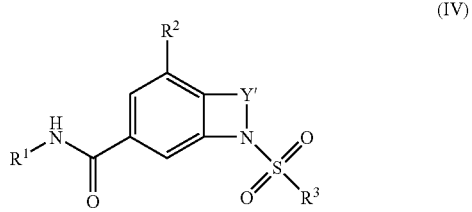

(IV)

Compounds of general formula (IV) can be accessed according to the general scheme 3:

Scheme 3

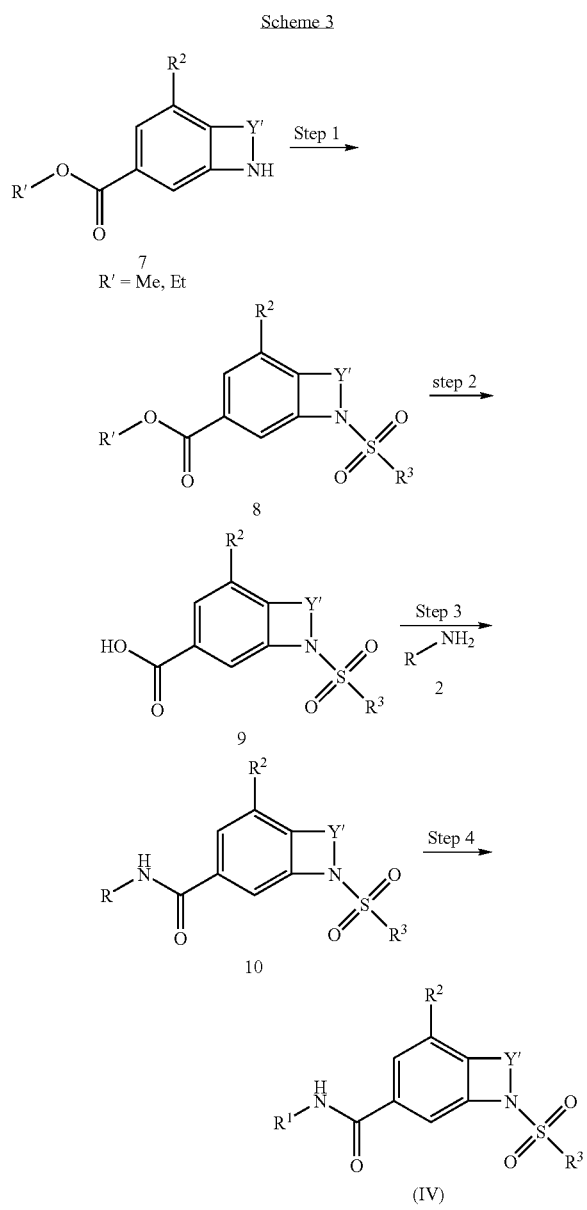

In step 1, scheme 3, carboxylic acid esters of general formula 7 are converted to sulfonamides 8 according to methods well known in the art, e.g. sulphonylation of amines with sulphonyl chlorides. The reaction is typically carried out in anhydrous solvents such as dichloromethane, tetrahydrofuran, acetonitrile, toluene and mixtures thereof or in the absence of solvent, at temperatures between 0° C. and 110° C., optionally in the presence of a base like triethylamine, diisopropylethylamine or pyridine. In step 2, scheme 3, the obtained compound of the formula 8 is converted into the corresponding carboxylic acid of the formula 9, using methods well known to someone skilled in the art, e.g. base mediated ester hydrolysis. The reaction is typically carried out in solvents such as water, methanol, tetrahydrofuran and mixtures thereof at temperatures between −20° C. and 120° C. Typical reagents are aqueous or anhydrous lithium hydroxide, lithium hydroxide monohydrate, sodium hydroxide, potassium hydroxide, sodium hydrogen carbonate, sodium carbonate, potassium hydrogen carbonate and potassium carbonate. In step 3, scheme 3, the carboxylic acid derivatives of the formula 9 are converted, with the appropriate amines 2, into the corresponding amide using methods well known to someone skilled in the art, e.g. amide formation using a coupling reagent. This is typically carried out in aprotic solvents such as dichloromethane, tetrahydrofuran, N,N-dimethylformamide, N-methylpyrrolidinone and mixtures thereof at temperatures between 0° C. and 60° C. in the presence or absence of a base such as triethylamine, N,N-diisopropylethylamine or 4-(dimethylamino)pyridine. Typically used coupling agents are N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate and bromo-tris-pyrrolidino-phosphonium hexafluorophosphate. Alternatively, such reaction can be performed in two steps involving first formation of the acyl halide derivative of 9 and subsequent coupling reaction with an appropriate amine in the presence of a base. Typically employed reagents for the formation of the acyl chloride are thionyl chloride, phosphorus pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropyl ethyl amine or N-methylmorpholine. The obtained acyl chloride can be isolated or reacted as such with an appropriate amine 2 in an aprotic solvent, like dichloromethane, tetrahydrofuran or acetone, in the presence of a base. Typical bases are triethylamine, N-methylmorpholine, pyridine, diisopropyl ethyl amine or dimethylaminopyridine or mixtures thereof. In step 4, scheme 3, the protected carboxylic acid embedded in the group R of structure 10 is deprotected to yield the final compounds of general formula (IV), in analogy to what described for scheme 1, step 3.

Carboxylic acid esters of general formula 7 where $Y'=\!=\!\!-C(R^4R^5)C(R^6R^7)-$ and $R^5=R^7=H$ or $Y=\!=\!\!-(R^4R^5)C(R^6R^7)C(R^8R^9)-$ and $R^5=R^7=R^9=H$ are prepared according to the general scheme 4.

Scheme 4

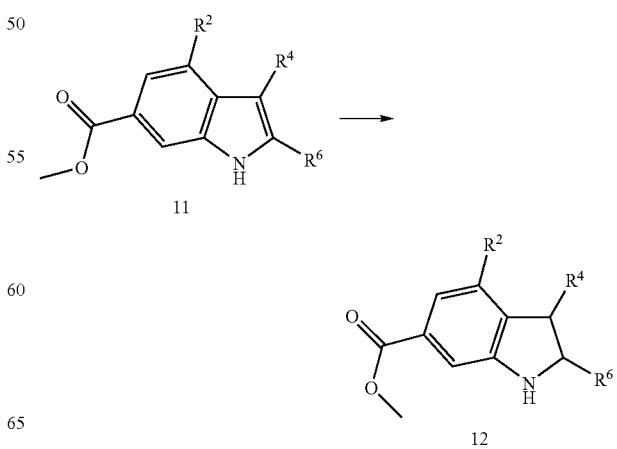

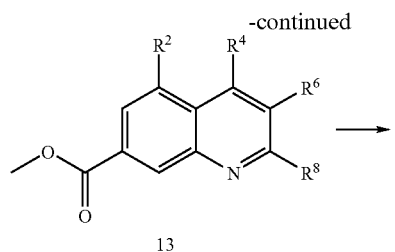

13

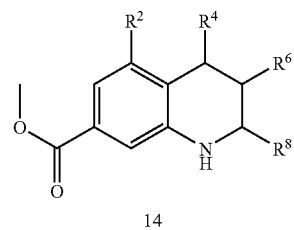

14

Substituted indole-6-carboxylic acid methyl ester 11 is converted into the corresponding 2,3-dihydroindole of formula 12, using methods well known to someone skilled in the art, e.g. indole reduction. The reaction is typically carried out in protic solvents such as acetic acid, trifluoroacetic acid, and mixtures thereof at temperatures between 0° C. and 30° C. Typically used reducing reagents are sodium cyanoborohydride, sodium triacetoxyborohydride and sodium borohydride.

Quinoline-7-carboxylic acid methyl esters 13 are converted into their corresponding 1,2,3,4-tetrahydroquinolines of the formula 14, using methods well known to someone skilled in the art, e.g. quinoline reduction. The reaction is typically carried out in solvents such as water, isopropanol, ethylene glycol, trifluoroacetic acid, tetrahydrofuran and mixtures thereof at temperatures between 20° C. and 160° C. with hydrogen or a hydrogen transfer reagent such as isopropanol in the presence or absence of a mineral acid such as perchloric acid or HCl. Typically used catalysts are polymer encapsulated palladium, pentamethylcyclopentadienyliridium(III) chloride dimer, Raney nickel, platinum oxide and other transition metal catalysts.

Compounds of general formula 7 wherein Y' is —C(R$^4$R$^5$)C(R$^6$R$^7$)C(R$^8$R$^9$)C(R$^{10}$R$^{11}$)— can be prepared starting from commercially available α-tetralone using methods well known to somebody skilled in the art. The aromatic ketone is brominated to 7-bromo-3,4-dihydro-2H-naphthalen-1-one using methods well known to somebody skilled in the art, i.e. aromatic electrophilic bromination. The reaction is carried out in a solvent, for example dichloromethane, at temperatures between 25° C. and 150° C. using elemental bromine as bromine source in the presence of a Lewis acid. Typically used Lewis acids are aluminum trichloride or aluminum tribromide. The obtained 7-bromo-3,4-dihydro-2H-naphthalen-1-one is converted to 8-bromo-1,3,4,5-tetrahydro-benzo[b]azepin-2-one using methods well known to somebody skilled in the art, i.e. Schmidt rearrangement. The reaction is carried out in a protic solvent, like for example acetic acid, in the presence of a nitrogen source, like for example ammonium azide, and an acid, like for example sulfuric acid. The obtained 8-bromo-1,3,4,5-tetrahydro-benzo[b]azepin-2-one is then reduced to 8-bromo-2,3,4,5-tetrahydro-1H-benzo[b]azepine using methods well known to somebody skilled in the art, i.e. amide reduction. The reaction is typically carried out in an ethereal solvent, like for example ether or tetrahydrofuran, using lithium aluminium hydride or diborane as reducing agents. The amino group of the obtained 8-bromo-2,3,4,5-tetrahydro-1H-benzo[b]azepine is then reacted with a sulfonyl chloride to form the corresponding sulfonamides, in analogy to what described above. The obtained 1-arylsulfonyl-8-bromo-2,3,4,5-tetrahydro-1H-benzo[b]azepines are converted to the corresponding 1-arylsulfonyl-2,3,4,5-tetrahydro-1H-benzo[b]azepine-8-carboxylic acid alkyl esters using methods well known to somebody skilled in the art, i.e. palladium catalysed alkoxycarbonylation. The reaction is typically carried out in an alcoholic solvent, like for example methanol, or in a mixture of an alcoholic solvent with an aprotic solvent, like toluene, at temperatures between 25° C. and 150° C. under an atmosphere of carbon monoxide at pressures between 1 atm and 100 atm or in the presence of an agent capable of liberating carbon monoxide under the reaction conditions, like for example molybdenum hexacarbonyl. Typically used palladium catalysts are palladium dichloride, palladium acetate, palladium tetrakis(triphenylphosphine) or palladium bis(dibenzylideneacetone). The obtained 1-arylsulfonyl-2,3,4,5-tetrahydro-1H-benzo[b]azepine-8-carboxylic acid alkyl esters are elaborated to final products of formula (IV) through hydrolysis and amide formation, in analogy to what described above.

Compounds of general formula (I) where Y is —C(R$^4$R$^5$)C(R$^6$R$^7$)C(R$^8$R$^9$)— and X is —C(O)NH— are part of the present invention and are represented by general formula (V):

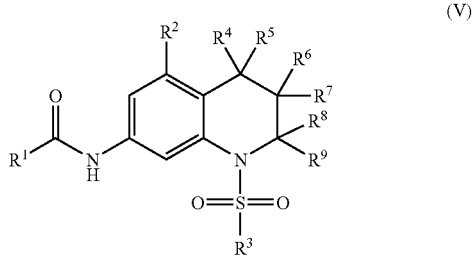

Compounds of general formula (V) can be accessed according to scheme 5:

Scheme 5

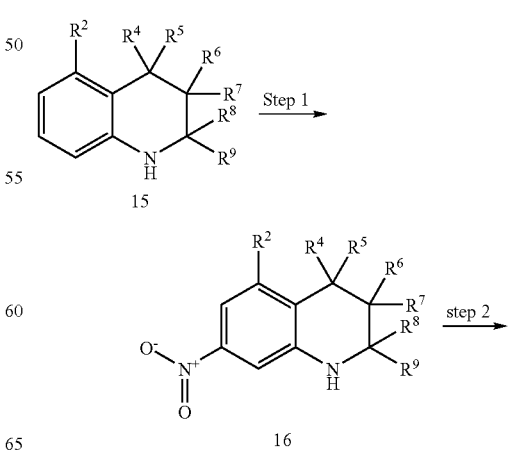

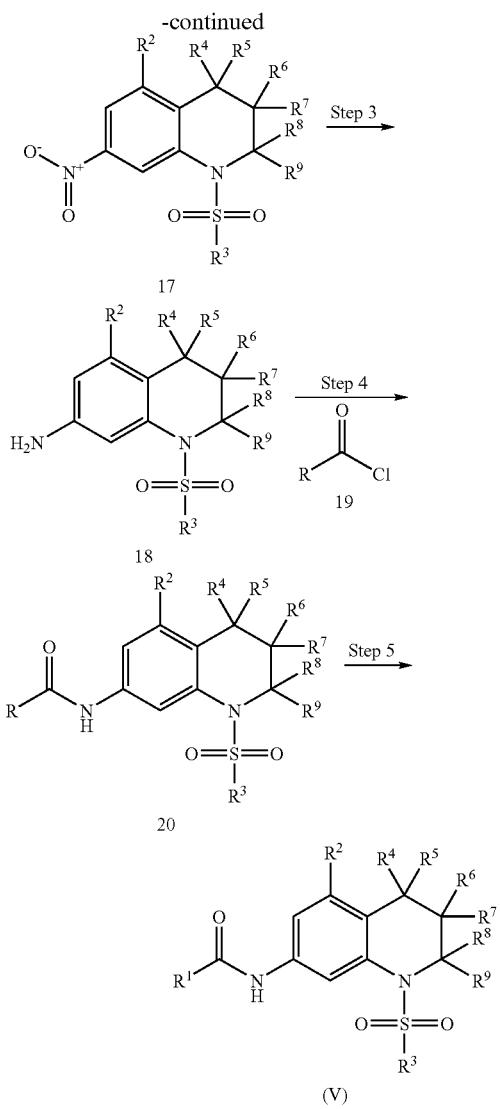

In step 1, scheme 5, tetrahydroquinolines of general formula 15 are converted to the nitro derivatives 16 according to methods well known in the art, e.g. electrophilic aromatic nitration. The reaction is typically carried out using nitric acid as a nitrating agent in the presence of a strong mineral acid, like, typically, sulfuric acid. In step 2, scheme 5, the obtained compounds of general formula 16 are converted to the corresponding sulfonamides of general formula 17, according to methods well known in the art, e.g. sulphonylation of amines with sulphonyl chlorides. The reaction is typically carried out in anhydrous solvents such as dichloromethane, tetrahydrofuran, acetonitrile, toluene and mixtures thereof or in the absence of solvent, at temperatures between 0° C. and 110° C., optionally in the presence of a base like triethylamine, diisopropylethylamine or pyridine. In step 3, scheme 5, the compounds of general formula 17 are converted to the corresponding amines 18 according to methods well known in the art, e.g. nitro reduction. The reaction is typically carried out in solvents such as ethanol, methanol, water under an atmosphere of hydrogen at a pressure of 1 to 50 bar and temperatures between 0° C. and 100° C. with catalysts such as palladium, platinum or platinum oxide. Alternatively, the reaction can be carried out using reducing metals like for example tin, tin chloride in the presence of concentrated mineral acids like hydrochloric or sulfuric acid, or with zinc metal in the presence of ammonium chloride. In step 4, scheme 5, the amines of general formula 18 are converted with appropriate acyl chlorides 19 into amides of general formula 20, according to methods well known to someone skilled in the art, e.g. amide coupling. The reaction is typically carried out in an aprotic solvent, like dichloromethane, tetrahydrofuran or acetone, in the presence of a base. Typical bases are triethylamine, N-methylmorpholine, pyridine, diisopropyl ethyl amine or dimethylaminopyridine or mixtures thereof. In step 5, scheme 5, the protected carboxylic acid embedded in the group R of structure 20 is deprotected to yield the final compounds of general formula (V), in analogy to what described for scheme 1, step 3.

Compounds of formula (I) which comprise an acid group such as COOH can form salts with physiologically compatible bases. Examples of such salts are alkaline, earth-alkaline and ammonium salts such as e.g. sodium, potassium, calcium and trimethylammonium salt. One method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention have been found to inhibit liver carnitine palmitoyl transferase 1 (L-CPT1) activity. The compounds of the present invention can therefore be used in the treatment and/or prophylaxis of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by L-CPT1 inhibitors, particularly as therapeutically active substances for the treatment and/or prophylaxis of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

In another preferred embodiment, the invention relates to a method for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure, which method comprises administering a compound as defined above to a human being or animal.

The invention also embraces the use of compounds as defined above for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention also relates to the use of compounds as described above for the preparation of medicaments for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure. Such medicaments comprise a compound as described above.

Prevention and/or treatment of hyperglycemia and non insulin dependent diabetes mellitus is the preferred indication.

The following tests were carried out in order to determine the activity of the compounds of the present invention. Background information on the performed assays can be found in: Jackson et al., 1999, *Biochem. J.* 341, 483-489 and Jackson et al., 2000, *J. Biol. Chem.* 275, 19560-19566.

Human liver and muscle CPT1 cDNAs and rat CPT2 cDNA were subcloned in pGAPZB or pGAPZA, respectively. These plasmids were used to transform *P. pastoris* strain X-33 via electroporation after the preparation of electrocompetent cells. High copy number clones were selected where necessary using 0.5 or 1 mg/ml Zeocin. Cultures for activity measurements were induced for 16 h in YPD medium (1% yeast extract, 2% peptone, 2% glucose). Crude cell extracts were prepared by disrupting the cells with glass beads or French Press, depending on fermenter sizes. After centrifugation, the cell-free extracts were resuspended in cell breaking buffer (50 mM Tris, pH 7.4, 100 mM KCl, 1 mM EDTA) in the presence of a protease inhibitor cocktail, before aliquoting and freezing at −20° C.

CPT activity was measured using a spectrophotometric assay using 5,5'-dithio-bis-(2-nitrobenzoic acid) (DTNB) also called Ellman's reagent. The HS-CoA released on the formation of acylcarnitine from carnitine (500 µM) and palmitoyl-CoA (80 µM) reduced DTNB (300 µM) forming 5-mercapto-(2-nitrobenzoic acid) which absorbed at 410 nm with a molar extinction coefficient of 13600 $M^{-1} \cdot cm^{-1}$. The assay buffer contained 120 mM KCl, 25 mM Tris, pH 7.4, 1 mM EDTA. This assay was used for the identification of selective inhibitors of the liver CPT1 isoform versus the muscle CPT1 and CPT2 isoforms.

The compounds according to formula (I) preferably have an $IC_{50}$ value below 10 µM, preferably 10 nM to 10 µM, more preferably 10 nM to 5 µM. The following table shows data for some examples.

| Example | L-CPT1 inhibition $IC_{50}$ [µmol/l] |
| --- | --- |
| 7 | 0.1251 |
| 14 | 0.2105 |
| 17 | 0.0472 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-200 mg, of a compound of formula I.

The following Examples serve to illustrate the present invention in more detail. They are, however, not intended to limit its scope in any manner.

EXAMPLES

Example 1

(4-{[1-(5-Chloro-2-methoxy-benzenesulfonyl)-1H-indole-6-carbonyl]-amino}-phenyl)-acetic acid Step 1. A solution of indole-6-carboxylic acid (2.00 g, 12.40 mmol) in dimethylformamide (20.00 mL) under argon was treated with N-methyl morpholine (6.82 mL, 62.04 mmol), O-(7-azabenzotriazol-1-yl)-N,N,N',N'-tetramethyluronium-hexaflurophophate (HATU) (7.08 g, 18.62 mmol) and (4-amino-phenyl)-acetic acid tert-butyl ester (2.57 g, 12.40 mmol). The mixture was warmed at 60° C. and stirred for 18 hours. After cooling to room temperature, water (15.00 mL) was added. The resulting slurry was extracted with ethyl acetate and the combined organic phases washed with brine, dried over magnesium sulphate and evaporated. The residue was purified by flash chromatography (heptane/ethyl acetate gradient), to yield pure {4-[(1H-indole-6-carbonyl)-amino]-phenyl}-acetic acid tert-butyl ester (0.51 g) and a mixture of {4-[(1H-indole-6-carbonyl)-amino]-phenyl}-acetic acid tert-butyl ester and 1H-indole-6-carboxylic acid [1,2,3]triazolo[4,5-b]pyridin-3-yl ester (3.41 g). This was dissolved in tetrahydrofuran (34.00 mL) and treated with 1N NaOH. The mixture was stirred at room temperature for 4 hours, then extracted with ethyl acetate. The combined organic phases were washed with brine, dried over magnesium sulphate and evaporated, and the residue triturated in ether to afford {4-[(1H-indole-6-carbonyl)-amino]-phenyl}-acetic acid tert-butyl ester (1.36 g), which was combined with the aliquot obtained by flash chromatography. Total yield of {4-[(1H-indole-6-carbonyl)-amino]-phenyl}-acetic acid tert-butyl ester, 1.87 g (43%), MS (mass spectrometry) (ISP): m/e=351.3 (M+H). As used herein (M+H)=the molecular weight of the compound plus a proton.

Step 2. A solution of {4-[(1H-indole-6-carbonyl)-amino]-phenyl}-acetic acid tert-butyl ester (0.20 g, 0.57 mmol) in toluene (2.90 mL) was treated with tetrabutylammonium hydrogensulfate (0.02 g, 0.05 mmol) and a 50% solution of NaOH in water (0.57 mL, 7.12 mmol). After stirring at room temperature for 5 min, 5-chloro-2-methoxybenzenesulfonyl chloride (0.21 g, 0.85 mmol) was added. The mixture was stirred for 2 hours, then poured over ice. The resulting slurry was extracted with ethyl acetate and the combined organic phases washed with brine, dried over magnesium sulphate and evaporated. The residue was purified by flash chromatography (heptane/ethyl acetate gradient) to yield (4-{[1-(5-chloro-2-methoxy-benzenesulfonyl)-1H-indole-6-carbonyl]-amino}-phenyl)-acetic acid tert-butyl ester as a light yellow oil, 0.26 g (81%), MS (ISP): m/e=555.2 (M+H).

Step 3. (4-{[1-(5-Chloro-2-methoxy-benzenesulfonyl)-1H-indole-6-carbonyl]-amino}-phenyl)-acetic acid tert-butyl ester (0.25 g, 0.46 mmol) was dissolved in 4M HCl in dioxane (4.00 mL) and stirred at room temperature for 18 hours. The volatiles were evaporated and the residue taken up in ethyl acetate/heptane 1:1 and sonicated. The solid was filtered washing with ethyl acetate/heptane 1:1 and dried under vacuum. (4-{[1-(5-Chloro-2-methoxy-benzenesulfonyl)-1H-indole-6-carbonyl]-amino}-phenyl)-acetic acid was obtained as an off-white solid, 0.14 g (63%), MS (ISP): m/e=497.1 (M–H).

Example 2

(4-{[1-(2-Methoxy-5-methyl-benzenesulfonyl)-1H-indole-6-carbonyl]-amino}-phenyl)-acetic acid The title compound was prepared as for example 1, steps 1 to 3. Step 2 was performed using 2-methoxy-5-methylbenzenesulfonyl chloride, and yielded (4-{[1-(2-methoxy-5-methyl-benzenesulfonyl)-1H-indole-6-carbonyl]-amino}-phenyl)-acetic acid tert-butyl ester, which was converted to (4-{[1-(2-methoxy-5-methyl-benzenesulfonyl)-1H-indole-6-carbonyl]-amino}-phenyl)-acetic acid in step 3. Off-white solid, yield: 0.13 g (73%), MS (ISP): m/e=477.1 (M–H).

Example 3

(4-{[1-(3,5-Dimethyl-benzenesulfonyl)-1H-indole-6-carbonyl]-amino}-phenyl)-acetic acid The title compound was prepared as for example 1, steps 1 to 3. Step 2 was performed using 3,5-dimethylbenzenesulfonyl chloride, and yielded (4-{[1-(3,5-dimethyl-benzenesulfonyl)-1H-indole-6-carbonyl]-amino}-phenyl)-acetic acid tert-butyl ester, which was converted to (4-{[1-(3,5-dimethyl-benzenesulfonyl)-1H-indole-6-carbonyl]-amino}-phenyl)-acetic acid in step 3. Off-white solid, yield: 0.11 g (49%), MS (ISP): m/e=461.4 (M–H).

Example 4

(4-{[1-(3-Chloro-benzenesulfonyl)-1H-indole-6-carbonyl]-amino}-phenyl)-acetic acid The title compound was prepared as for example 1, steps 1 to 3. Step 2 was performed using 3-chlorobenzenesulfonyl chloride, and yielded (4-{[1-(3-chloro-benzenesulfonyl)-1H-indole-6-carbonyl]-amino}-phenyl)-acetic acid tert-butyl ester, which was converted to (4-{[1-(3-chloro-benzenesulfonyl)-1H-indole-6-carbonyl]-amino}-phenyl)-acetic acid in step 3. White solid, yield: 0.20 g (99%), MS (ISP): m/e=467.3 (M–H).

Example 5

(4-{[1-(2-Methoxy-5-methyl-benzenesulfonyl)-2,3-dihydro-1H-indole-6-carbonyl]-amino}-phenyl)-acetic acid Step 1. A solution of {4-[(1H-indole-6-carbonyl)-amino]-phenyl}-acetic acid tert-butyl ester (see example 1, step 1) (0.50 g, 1.43 mmol) in acetic acid (5.00 mL) was treated at room temperature with sodium cyanoborohydride (0.28 g, 4.50 mmol) and stirred for 1 hour. A further aliquot of sodium cyanoborohydride (0.09 g, 1.49 mmol) was added, and the mixture stirred for 1 hour. A further aliquot of sodium cyanoborohydride (0.19 g, 3.01 mmol) was added and the mixture stirred for further 15 min. The mixture was treated with water and a 2N NaOH solution and extracted with ethyl acetate. The combined organic phases were dried over magnesium sulphate and evaporated. The residue is crude {4-[(2,3-dihydro-1H-indole-6-carbonyl)-amino]-phenyl}-acetic acid tert-butyl ester, which is used as such in the following reaction.

Step 2. Crude {4-[(2,3-dihydro-1H-indole-6-carbonyl)-amino]-phenyl}-acetic acid tert-butyl ester (0.17 g, 0.48 mmol) was dissolved in pyridine (0.40 mL) and treated with 2-methoxy-5-methylbenzenesulfonyl chloride (0.12 g, 0.52 mmol). The mixture was stirred at room temperature for 1 hour, then quenched with 1N citric acid. The mixture was extracted with ethyl acetate and the combined organic phases dried over magnesium sulphate and evaporated. The residue was purified by flash chromatography (heptane/ethyl acetate gradient) to yield 4-{[1-(2-methoxy-5-methyl-benzenesulfonyl)-2,3-dihydro-1H-indole-6-carbonyl]-amino}-phenyl)-acetic acid tert-butyl ester as an off-white solid, 0.13 g (51%), MS (ISP): m/e=537.5 (M+H).

Step 3. 4-{[1-(2-Methoxy-5-methyl-benzenesulfonyl)-2,3-dihydro-1H-indole-6-carbonyl]-amino}-phenyl)-acetic acid tert-butyl ester (0.13 g, 0.24 mmol) was dissolved in 4M HCl in dioxane (2.00 mL) and stirred at room temperature for 18 hours. The volatiles were evaporated and the residue taken up in ethyl acetate and sonicated. The solid was filtered washing with ethyl acetate and dried under vacuum. 4-{[1-(2-Methoxy-5-methyl-benzenesulfonyl)-2,3-dihydro-1H-indole-6-carbonyl]-amino}-phenyl)-acetic acid was obtained as an off-white solid, 0.06 g (52%), MS (ISP): m/e=479.1 (M−H).

Example 6

(4-{[1-(3,5-Dimethyl-benzenesulfonyl)-2,3-dihydro-1H-indole-6-carbonyl]-amino}-phenyl)-acetic acid The title compound was prepared as for example 5, steps 1 to 3. Step 2 was performed using 3,5-dimethylbenzenesulfonyl chloride, and yielded (4-{[1-(3,5-dimethyl-benzenesulfonyl)-2,3-dihydro-1H-indole-6-carbonyl]-amino}-phenyl)-acetic acid tert-butyl ester, which was converted to (4-{[1-(3,5-dimethyl-benzenesulfonyl)-2,3-dihydro-1H-indole-6-carbonyl]-amino}-phenyl)-acetic acid in step 3. Off-white solid, yield: 0.10 g (94%), MS (ISP): m/e=463.1 (M−H).

Example 7

(4-{[1-(3-Chloro-benzenesulfonyl)-2,3-dihydro-1H-indole-6-carbonyl]-amino}-phenyl)-acetic acid The title compound was prepared as for example 5, steps 1 to 3. Step 2 was performed using 3-chlorobenzenesulfonyl chloride, and yielded (4-{[1-(3-chloro-benzenesulfonyl)-2,3-dihydro-1H-indole-6-carbonyl]-amino}-phenyl)-acetic acid tert-butyl ester, which was converted to (4-{[1-(3-chloro-benzenesulfonyl)-2,3-dihydro-1H-indole-6-carbonyl]-amino}-phenyl)-acetic acid in step 3. White solid, yield: 0.12 g (92%), MS (ISP): m/e=469.1 (M−H).

Example 8

(2-{[1-(3,5-Dimethyl-benzenesulfonyl)-2,3-dihydro-1H-indole-6-carbonyl]-amino}-thiazol-4-yl)-acetic acid Step 1. A solution of 2,3-dihydro-1H-indole-6-carboxylic acid methyl ester (0.23 g, 1.30 mmol) in pyridine (0.60 mL) was treated with 3,5-dimethylbenzenesulfonyl chloride (0.30 g, 1.47 mmol) and stirred at room temperature for 2 hours. The mixture was diluted with 1N HCl and extracted with dichloromethane. The combined organic phases were washed with brine, dried over magnesium sulphate and evaporated. The residue was taken up in heptane/ethyl acetate 1:1 and filtered. The filtrate was pure 1-(3,5-dimethyl-benzenesulfonyl)-2,3-dihydro-1H-indole-6-carboxylic acid methyl ester, 0.41 g (92%), MS (ISP): m/e=346.3 (M+H).

Step 2. 1-(3,5-Dimethyl-benzenesulfonyl)-2,3-dihydro-1H-indole-6-carboxylic acid methyl ester (0.40 g, 1.17 mmol) was suspended in ethanol (2.00 mL) and treated with 3N KOH in water (1.17 mL, 3.51 mmol). The mixture was warmed at 50° C. and stirred for 1 hour, then warmed at 70° C. and stirred for 20 min. After cooling to room temperature, the volatiles were evaporated. The residue was dissolved in water (1.00 mL) and the pH set to 1 with 2N HCl. The precipitate was filtered, washing with water, then dried under high vacuum. 1-(3,5-Dimethyl-benzenesulfonyl)-2,3-dihydro-1H-indole-6-carboxylic acid was obtained as an off-white solid, 0.38 g (98%), MS (ISP): m/e=330.3 (M−H).

Step 3. A solution of 1-(3,5-dimethyl-benzenesulfonyl)-2,3-dihydro-1H-indole-6-carboxylic acid (0.20 g, 0.60 mmol) in dimethylformamide (1.00 mL) under argon was treated with N-methyl morpholine (0.31 g, 0.33 mL, 3.01 mmol), HATU (0.34 g, 0.90 mmol) and (2-amino-thiazol-4-yl)-acetic acid ethyl ester (0.17 g, 0.91 mmol). The mixture was stirred at room temperature for 30 min, then treated with 4-dimethylaminopyridine (0.07 g, 0.60 mmol). The mixture was warmed to 60° C. and stirred for 50 hours. After cooling to room temperature the mixture was partitioned between water and ethyl acetate. The organic phase was washed with brine, dried over magnesium sulphate and evaporated. The residue was purified via flash chromatography (heptane/ethyl acetate gradient) to yield (2-{[1-(3,5-dimethyl-benzenesulfonyl)-2,3-dihydro-1H-indole-6-carbonyl]-amino}-thiazol-4-yl)-acetic acid ethyl ester as an off-white solid, 0.10 g (35%), MS (ISP): m/e=500.4 (M+H).

Step 4. (2-{[1-(3,5-Dimethyl-benzenesulfonyl)-2,3-dihydro-1H-indole-6-carbonyl]-amino}-thiazol-4-yl)-acetic acid ethyl ester (0.10 g, 0.20 mmol) was suspended in ethanol (1.00 mL) and treated at room temperature with 3N KOH in water (0.20 mL, 0.60 mmol). The mixture was warmed to 50° C. and stirred for 18 hours, then cooled to room temperature and evaporated. The residue was dissolved in water (1.00 mL) and set to pH 1 with HCl 1N. The resulting suspension was filtered, washing with water and the filtrate dried under vacuum to yield (2-{[1-(3,5-dimethyl-benzenesulfonyl)-2,3-dihydro-1H-indole-6-carbonyl]-amino}-thiazol-4-yl)-acetic acid as a white solid, 0.09 g (99%), MS (ISP): m/e=470.2 (M−H).

2,3-Dihydro-1H-indole-6-carboxylic acid methyl ester was Obtained as Follows

A solution of indole-6-carboxylic acid methyl ester (534 mg, 3.05 mmol) in acetic acid (7.5 ml) was cooled to 0° C. Sodium cyanoborohydride (580 mg, 9.2 mmol, 3 equiv.) was added and the mixture stirred at 15° C. for 40 min. A further aliquot of sodium cyanoborohydride (193 mg, 3.05 mmol, 1 equiv.) was added, and the reaction mixture was stirred for 30 min. at room temperature. The solvent was then evaporated, and the residue dissolved in dichloromethane and washed with 1N NaOH. The organic phase was dried with $Na_2SO_4$ and evaporated, yielding 2,3-dihydro-1H-indole-6-carboxylic acid methyl ester as a light yellow solid, 494 mg (77%). This was used as such in the following reaction.

Example 9

(2-{[1-(3-Chloro-benzenesulfonyl)-2,3-dihydro-1H-indole-6-carbonyl]-amino}-thiazol-4-yl)-acetic acid The title compound was prepared as for example 8, steps 1 to 4. Step 1 was performed using 3-chlorobenzensulfonyl chloride and yielded 1-(3-chloro-benzenesulfonyl)-2,3-dihydro-1H-indole-6-carboxylic acid methyl ester) which was hydrolyzed to 1-(3-chloro-benzenesulfonyl)-2,3-dihydro-1H-indole-6-carboxylic acid in step 2 and coupled to (2-amino-thiazol-4-yl)-acetic acid ethyl ester in step 3 to yield (2-{[1-(3-chloro-benzenesulfonyl)-2,3-dihydro-1H-indole-6-carbonyl]-amino}-thiazol-4-yl)-acetic acid ethyl ester. This was hydrolyzed to (2-{[1-(3-chloro-benzenesulfonyl)-2,3-dihydro-1H-indole-6-carbonyl]-amino}-thiazol-4-yl)-acetic acid in step 4: white solid, 0.08 g (96%), MS (ISP): m/e=476.0 (M–H).

Example 10

(4-{[1-(5-Chloro-2-methoxy-benzenesulfonyl)-2,3-dihydro-1H-indole-6-carbonyl]-amino}-phenyl)-acetic acid The title compound was prepared as for example 8, steps 1 to 4. Step 1 was performed using 5-chloro-2-methoxybenzensulfonyl chloride and yielded 1-(5-chloro-2-methoxybenzenesulfonyl)-2,3-dihydro-1H-indole-6-carboxylic acid methyl ester, which was hydrolyzed to 1-(5-chloro-2-methoxy-benzenesulfonyl)-2,3-dihydro-1H-indole-6-carboxylic acid in step 2 and coupled to (4-amino-phenyl)-acetic acid ethyl ester and yielded (4-{[1-(5-chloro-2-methoxy-benzenesulfonyl)-2,3-dihydro-1H-indole-6-carbonyl]-amino}-phenyl)-acetic acid ethyl ester, which was hydrolyzed to (4-{[1-(5-chloro-2-methoxy-benzenesulfonyl)-2,3-dihydro-1H-indole-6-carbonyl]-amino}-phenyl)-acetic acid in step 4, MS (ISP): m/e=499.1 (M–H).

Example 11

(2-{[1-(5-Chloro-2-methoxy-benzenesulfonyl)-2,3-dihydro-1H-indole-6-carbonyl]-amino}thiazol-4-yl)-acetic acid 1-(5-Chloro-2-methoxy-benzenesulfonyl)-2,3-dihydro-1H-indole-6-carboxylic acid was converted to the title compound in analogy to example 8, steps 3 and 4. Step 3 was performed using (2-amino-thiazol-4-yl)-acetic acid ethyl ester and yielded (2-{[1-(5-chloro-2-methoxy-benzenesulfonyl)-2,3-dihydro-1H-indole-6-carbonyl]-amino}-thiazol-4-yl)-acetic acid ethyl ester, which was hydrolyzed to (2-{[1-(5-chloro-2-methoxy-benzenesulfonyl)-2,3-dihydro-1H-indole-6-carbonyl]-amino}-thiazol-4-yl)-acetic acid in step 4, MS (ISP): m/e=506.1 (M–H).

Example 12

(2-{[1-(5-Chloro-2-methoxy-benzenesulfonyl)-2,3-dihydro-1H-indole-6-carbonyl]-amino}-5-methyl-thiazol-4-yl)-acetic acid 1-(5-Chloro-2-methoxy-benzenesulfonyl)-2,3-dihydro-1H-indole-6-carboxylic acid was converted to the title compound in analogy to example 8, steps 3 and 4. Step 3 was performed using (2-amino-5-methyl-thiazol-4-yl)-acetic acid methyl ester and yielded (2-{[1-(5-chloro-2-methoxy-benzenesulfonyl)-2,3-dihydro-1H-indole-6-carbonyl]-amino}-5-methyl-thiazol-4-yl)-acetic acid methyl ester, which was hydrolyzed to (2-{[1-(5-chloro-2-methoxy-benzenesulfonyl)-2,3-dihydro-1H-indole-6-carbonyl]-amino}-5-methyl-thiazol-4-yl)-acetic acid in step 4, MS (ISP): m/e=520.1 (M–H).

Example 13

(3-{[1-(5-Chloro-2-methoxy-benzenesulfonyl)-2,3-dihydro-1H-indole-6-carbonyl]-amino}-pyrazol-1-yl)-acetic acid 1-(5-Chloro-2-methoxy-benzenesulfonyl)-2,3-dihydro-1H-indole-6-carboxylic acid was converted to the title compound in analogy to example 8, steps 3 and 4. Step 3 was performed using (3-amino-pyrazol-1-yl)-acetic acid ethyl ester and yielded (3-{[1-(5-chloro-2-methoxy-benzenesulfonyl)-2,3-dihydro-1H-indole-6-carbonyl]-amino}-pyrazol-1-yl)-acetic acid ethyl ester, which was hydrolyzed to 3-{[1-(5-chloro-2-methoxy-benzenesulfonyl)-2,3-dihydro-1H-indole-6-carbonyl]-amino}-pyrazol-1-yl)-acetic acid in step 4, MS (ISP): m/e=489.1 (M–H).

Example 14

(4-{[1-(5-Chloro-2-methoxy-benzenesulfonyl)-4-methyl-2,3-dihydro-1H-indole-6-carbonyl]-amino}-phenyl)-acetic acid 1-(5-Chloro-2-methoxy-benzenesulfonyl)-4-methyl-2,3-dihydro-1H-indole-6-carboxylic acid was converted to the title compound in analogy to example 8, steps 3 and 4. Step 3 was performed using (4-amino-phenyl)-acetic acid ethyl ester and yielded (4-{[1-(5-chloro-2-methoxy-benzenesulfonyl)-4-methyl-2,3-dihydro-1H-indole-6-carbonyl]-amino}-phenyl)-acetic acid ethyl ester, which was hydrolyzed to (4-{[1-(5-chloro-2-methoxy-benzenesulfonyl)-4-methyl-2,3-dihydro-1H-indole-6-carbonyl]-amino}-phenyl)-acetic acid in step 4, MS (ISP): m/e=515.3 (M+H).

Example 15

(2-{[1-(5-Chloro-2-methoxy-benzenesulfonyl)-4-methyl-2,3-dihydro-1H-indole-6-carbonyl]-amino}-thiazol-4-yl)-acetic acid 1-(5-Chloro-2-methoxy-benzenesulfonyl)-4-methyl-2,3-dihydro-1H-indole-6-carboxylic acid was converted to the title compound in analogy to example 8, steps 3 and 4. Step 3 was performed using (2-amino-thiazol-4-yl)-acetic acid ethyl ester and yielded (2-{[1-(5-chloro-2-methoxy-benzenesulfonyl)-4-methyl-2,3-dihydro-1H-indole-6-carbonyl]-amino}-thiazol-4-yl)-acetic acid ethyl ester, which was hydrolyzed to (2-{[1-(5-chloro-2-methoxy-benzenesulfonyl)-4-methyl-2,3-dihydro-1H-indole-6-carbonyl]-amino}-thiazol-4-yl)-acetic acid in step 4, MS (ISP): m/e=522.3 (M+H).

Example 16

(2-{[1-(5-Chloro-2-methoxy-benzenesulfonyl)-2,3,4,5-tetrahydro-1H-benzo[b]azepine-8-carbonyl]-amino}-thiazol-4-yl)-acetic acid 1-(5-Chloro-2-methoxy-benzenesulfonyl)-2,3,4,5-tetrahydro-1H-benzo[b]azepine-8-carboxylic acid was converted to the title compound in analogy to example 8, steps 3 and 4. Step 3 was performed using (2-amino-thiazol-4-yl)-acetic acid ethyl ester and 1-(5-chloro-2-methoxy-benzenesulfonyl)-2,3,4,5-tetrahydro-1H-benzo[b]azepine-8-carboxylic acid and yielded (2-{[1-(5-chloro-2-methoxy-benzenesulfonyl)-2,3,4,5-tetrahydro-1H-benzo[b]azepine-8-carbonyl]-amino}-thiazol-4-yl)-acetic acid ethyl ester, which was hydrolyzed to (2-{[1-(5-chloro-2-methoxy-benzenesulfonyl)-2,3,4,5-tetrahydro-1H-benzo[b]azepine-8-carbonyl]-amino}-thiazol-4-yl)-acetic acid in step 4, MS (ISP): m/e=536.1 (M+H).

1-(5-Chloro-2-methoxy-benzenesulfonyl)-2,3,4,5-tetrahydro-1H-benzo[b]azepine-8-carboxylic acid was obtained according to the following procedure:

Step 1. Borane tetrahydrofuran complex (1 M solution in tetrahydrofuran, 21 mL, 21 mmol) was added to a solution of 8-bromo-1,3,4,5-tetrahydro-benzo[b]azepin-2-one (prepared from 7-bromo-3,4-dihydro-2H-naphthalen-1-one in analogy with the general procedure described in *J Chem. Soc.* (C) 1969, 183; 1.00 g, 4.17 mmol) in tetrahydrofuran, and the solution was heated at reflux for 2 h. After cooling, methanol (21 mL) was added, and volatile material was removed by distillation. The residue was taken up in 5% ethanolic sulfuric acid solution (12 mL) and heated at reflux for 2 h, then basified to pH 10 by addition of 2 M aq. sodium hydroxide solution and partitioned between water and ethyl acetate. The organic layer was dried (MgSO$_4$) and evaporated. Chromatography (SiO$_2$, heptane-ethyl acetate 2:1) yielded 8-bromo-2,3,4,5-tetrahydro-1H-benzo[b]azepine (865 mg, 92%). White solid, MS (ISP) m/e=226.1 (M+H).

Step 2. 8-Bromo-2,3,4,5-tetrahydro-1H-benzo[b]azepine was reacted with 5-chloro-2-methoxybenzenesulfonyl chloride in analogy to example 34, step 2, yielding 8-bromo-1-(5-chloro-2-methoxy-benzenesulfonyl)-2,3,4,5-tetrahydro-1H-benzo[b]azepine. Off-white solid, MS (ISP): m/e 430.2 (M+H).

Step 3. A solution of 8-bromo-1-(5-chloro-2-methoxy-benzenesulfonyl)-2,3,4,5-tetrahydro-1H-benzo[b]azepine (1.20 g, 2.78 mmol), triethylamine (703 mg, 6.96 mmol), and dichloro[1,1'-bis(diphenylphosphine)ferrocene]palladium (II) dichloromethane complex (120 mg, 0.278 mmol) in toluene (6 mL) and methanol (6 mL) was heated at 110° C. under a carbon monoxide atmosphere (100 bar) for 18 h, then the reaction mixture was concentrated. Chromatography of the residue (SiO$_2$, heptane-ethyl acetate 2:1) yielded 1-(5-chloro-2-methoxy-benzenesulfonyl)-2,3,4,5-tetrahydro-1H-benzo[b]azepine-8-carboxylic acid methyl ester (709 mg, 62%). White solid, MS (ISP): m/e 410.1 (M+H).

Step 4. 1-(5-Chloro-2-methoxy-benzenesulfonyl)-2,3,4,5-tetrahydro-1H-benzo[b]azepine-8-carboxylic acid methyl ester was hydrolyzed in analogy to example 34, step 3, yielding 1-(5-chloro-2-methoxy-benzenesulfonyl)-2,3,4,5-tetrahydro-1H-benzo[b]azepine-8-carboxylic acid. Light yellow solid, MS (ISP): m/e 394.1 (M−H).

Example 17

(4-{[1-(2-Methoxy-5-methyl-benzenesulfonyl)-1,2,3,4-tetrahydro-quinoline-7-carbonyl]-amino}-phenyl)-acetic acid Step 1. A solution of 1,2,3,4-tetrahydro-quinoline-7-carboxylic acid methyl ester (23.00 g, 0.12 mol) in dichloromethane (0.70 L) and pyridine (0.10 L) was treated with 2-methoxy-5-methyl-benzenesulfonyl chloride (31.78 g, 0.14 mol) and the mixture stirred at room temperature for 18 hours. The reaction mixture was then washed with 0.5 N HCl (0.40 L), water (2 times 0.40 L) and brine (0.25 L) and the organic phase dried over sodium sulphate and evaporated. The residue was sonicated in ether/dichloromethane 95:5 and the precipitate filtered and dried under vacuum. 1-(2-Methoxy-5-methyl-benzenesulfonyl)-1,2,3,4-tetrahydro-quinoline-7-carboxylic acid methyl ester was obtained as an off-white solid, 42.05 g (93%), MS (ISP): m/e=376.4 (M+H).

Step 2. A suspension of 1-(2-methoxy-5-methyl-benzenesulfonyl)-1,2,3,4-tetrahydro-quinoline-7-carboxylic acid methyl ester (35.09 g, 0.09 mol) in methanol (0.27 L) and tetrahydrofuran (95.00 mL) was treated with a 3N solution of KOH in water (93.00 mL, 0.28 mol) and stirred at room temperature for 18 hours, then at 45° C. for 2 hours. The organic solvents were evaporated and the residual aqueous slurry diluted with water (0.45 L) and cooled to 0° C. The mixture was set to pH 1 with HCl 3N (85.00 mL) and the precipitated solid was filtered and dried under vacuum. 1-(2-Methoxy-5-methyl-benzenesulfonyl)-1,2,3,4-tetrahydro-quinoline-7-carboxylic acid was obtained as an off-white solid, 34.08 g (100%), MS (ISP): m/e=360.1 (M−H).

1-(2-Methoxy-5-methyl-benzenesulfonyl)-1,2,3,4-tetrahydro-quinoline-7-carboxylic acid was converted to the title compound in analogy to example 8, steps 3 and 4. Step 3 was performed using (4-amino-phenyl)-acetic acid ethyl ester and yielded (4-{[1-(2-methoxy-5-methyl-benzenesulfonyl)-1,2,3,4-tetrahydro-quinoline-7-carbonyl]-amino}-phenyl)-acetic acid ethyl ester, which was hydrolyzed to (4-{[1-(2-methoxy-5-methyl-benzenesulfonyl)-1,2,3,4-tetrahydro-quinoline-7-carbonyl]-amino}-phenyl)-acetic acid in step 4, MS (ISP): m/e=493.4 (M−H).

1,2,3,4-Tetrahydro-quinoline-7-carboxylic acid methyl ester was obtained as follows: To a solution of his (pentamethyl-cyclopentadiene iridium dichloride) (32 mg, 0.02 equiv.) in a degassed mixture of isopropanol (9.5 ml) and water (0.5 ml) was added quinoline-7-carboxylic acid methyl ester (374 mg, 2.00 mmol) and perchloric acid (70% in water, 0.02 ml, 0.1 equiv.). The mixture was stirred at 85° C. for 17 hours, then the solvents were evaporated. The residue was purified by flash chromatography (heptane/ethyl acetate gradient), yielding 1,2,3,4-tetrahydro-quinoline-7-carboxylic acid methyl ester as a white solid, 305 mg (80%). MS (ISP): m/e=192.4 (M+H$^+$); $\delta_H$ (300 MHz; CDCl$_3$) 7.23 (1H, d), 7.13 (1H, s), 6.98 (1H, d), 3.86 (3H, s), 2.52 (2H, m), 3.32 (2H, t), 2.79 (2H, t), 1.94 (2H, m).

Example 18

(5-{[1-(2-Methoxy-5-methyl-benzenesulfonyl)-1,2,3,4-tetrahydro-quinoline-7-carbonyl]-amino}-[1,2,4]thiadiazol-3-yl)-acetic acid 1-(2-Methoxy-5-methyl-benzenesulfonyl)-1,2,3,4-tetrahydro-quinoline-7-carboxylic acid was converted to the title compound in analogy to example 8, steps 3 and 4. Step 3 was performed using (5-amino-[1,2,4]thiadiazol-3-yl)-acetic acid allyl ester and 1-(2-methoxy-5-methyl-benzenesulfonyl)-1,2,3,4-tetrahydro-quinoline-7-carboxylic acid and yielded (5-{[1-(2-methoxy-5-methyl-benzenesulfonyl)-1,2,3,4-tetrahydro-quinoline-7-carbonyl]-amino}-[1,2,4]thiadiazol-3-yl)-acetic acid allyl ester, which was hydrolyzed to (5-{[1-(2-methoxy-5-methyl-benzenesulfonyl)-1,2,3,4-tetrahydro-quinoline-7-carbonyl]-amino}-[1,2,4]thiadiazol-3-yl)-acetic acid in step 4, MS (ISP): m/e=501.1 (M−H).

Example 19

Hydroxy-(4-{[1-(2-methoxy-5-methyl-benzenesulfonyl)-1,2,3,4-tetrahydro-quinoline-7-carbonyl]-amino}-phenyl)-acetic acid 1-(2-Methoxy-5-methyl-benzenesulfonyl)-1,2,3,4-tetrahydro-quinoline-7-carboxylic acid was converted to the title compound in analogy to example 8, steps 3 and 4. Step 3 was performed using (4-amino-phenyl)-hydroxy-acetic acid methyl ester and 1-(2-methoxy-5-methyl-benzenesulfonyl)-1,2,3,4-tetrahydro-quinoline-7-carboxylic acid and yielded hydroxy-(4-{[1-(2-methoxy-5-methyl-benzenesulfonyl)-1,2,3,4-tetrahydro-quinoline-7-carbonyl]-amino}-phenyl)-acetic acid methyl ester, which was hydrolyzed to hydroxy-(4-{[1-(2-methoxy-5-methyl-benzenesulfonyl)-1,2,3,4-tetrahydro-quinoline-7-carbonyl]-amino}-phenyl)-acetic acid in step 4, MS (ISP): m/e=509.5 (M−H).

Example 20

2-{[1-(2-Methoxy-5-methyl-benzenesulfonyl)-1,2,3,4-tetrahydro-quinoline-7-carbonyl]-amino}-5,6-dihydro-4H-cyclopentathiazole-4-carboxylic acid 1-(2-Methoxy-5-methyl-benzenesulfonyl)-1,2,3,4-tetrahydro-quinoline-7-carboxylic acid was converted to the title compound in analogy to example 8, steps 3 and 4. Step 3 was performed using 2-amino-5,6-dihydro-4H-cyclopentathiazole-4-carboxylic acid ethyl ester and 1-(2-methoxy-5-methyl-benzenesulfonyl)-1,2,3,4-tetrahydro-7-quinoline-7-carboxylic acid and yielded 2-{[1-(2-methoxy-5-methyl-benzenesulfonyl)-1,2,3,4-tetrahydro-quinoline-7-carbonyl]-amino}-5,6-dihydro-4H-cyclopentathiazole-4-carboxylic acid ethyl ester, which was hydrolyzed to 2-{[1-(2-methoxy-5-methyl-benzenesulfonyl)-1,2,3,4-tetrahydro-quinoline-7-carbonyl]-amino}-5,6-dihydro-4H-cyclopentathiazole-4-carboxylic acid in step 4, MS (ISP): m/e=526.2 (M−H).

Example 21

(2-{[1-(2-Methoxy-5-methyl-benzenesulfonyl)-1,2,3,4-tetrahydro-quinoline-7-carbonyl]-amino}-thiazol-4-yl)-acetic acid 1-(2-Methoxy-5-methyl-benzenesulfonyl)-1,2,3,4-tetrahydro-quinoline-7-carboxylic acid was converted to the title compound in analogy to example 8, steps 3 and 4. Step 3 was performed using (2-amino-thiazol-4-yl)-acetic acid ethyl ester and 1-(2-methoxy-5-methyl-benzenesulfonyl)-1,2,3,4-tetrahydro-quinoline-7-carboxylic acid and yielded (2-{[1-(2-methoxy-5-methyl-benzenesulfonyl)-1,2,3,4-tetrahydro-quinoline-7-carbonyl]-amino}-thiazol-4-yl)-acetic acid ethyl ester, which was hydrolyzed to (2-{[1-(2-methoxy-5-methyl-benzenesulfonyl)-1,2,3,4-tetrahydro-quinoline-7-carbonyl]-amino}-thiazol-4-yl)-acetic acid in step 4, MS (ISP): m/e=502.0 (M+H).

Example 22

2-(4-{[1-(2-Methoxy-5-methyl-benzenesulfonyl)-1,2,3,4-tetrahydro-quinoline-7-carbonyl]amino}-phenyl)-propionic acid 1-(2-Methoxy-5-methyl-benzenesulfonyl)-1,2,3,4-tetrahydro-quinoline-7-carboxylic acid was converted to the title compound in analogy to example 8, steps 3 and 4. Step 3 was performed using 2-(4-amino-phenyl)-propionic acid methyl ester and 1-(2-methoxy-5-methyl-benzenesulfonyl)-1,2,3,4-tetrahydro-quinoline-7-carboxylic acid and yielded 2-(4-{[1-(2-methoxy-5-methyl-benzenesulfonyl)-1,2,3,4-tetrahydro-quinoline-7-carbonyl]-amino}-phenyl)-propionic acid methyl ester, which was hydrolyzed to 2-(4-{[1-(2-methoxy-5-methyl-benzenesulfonyl)-1,2,3,4-tetrahydro-quinoline-7-carbonyl]-amino}-phenyl)-propionic acid in step 4, MS (ISP): m/e=526.2 (M−H).

Example 23

2-{[1-(2-Methoxy-5-methyl-benzenesulfonyl)-1,2,3,4-tetrahydro-quinoline-7-carbonyl]-amino}-4,5,6,7-tetrahydro-benzothiazole-4-carboxylic acid 1-(2-Methoxy-5-methyl-benzenesulfonyl)-1,2,3,4-tetrahydro-quinoline-7-carboxylic acid was converted to the title compound in analogy to example 8, steps 3 and 4. Step 3 was performed using 2-amino-4,5,6,7-tetrahydro-benzothiazole-4-carboxylic acid ethyl ester and 1-(2-methoxy-5-methyl-benzenesulfonyl)-1,2,3,4-tetrahydro-quinoline-7-carboxylic acid and yielded 2-{[1-(2-methoxy-5-methyl-benzenesulfonyl)-1,2,3,4-tetrahydro-quinoline-7-carbonyl]-amino}-4,5,6,7-tetrahydro-benzothiazole-4-carboxylic acid ethyl ester, which was hydrolyzed to 2-{[1-(2-methoxy-5-methyl-benzenesulfonyl)-1,2,3,4-tetrahydro-quinoline-7-carbonyl]-amino}-4,5,6,7-tetrahydro-benzothiazole-4-carboxylic acid in step 4, MS (ISP): m/e=540.3 (M−H).

Example 24

{4-[1-(5-Chloro-2-methoxy-benzenesulfonyl)-1,2,3,4-tetrahydro-quinolin-7-ylcarbamoyl]-phenyl}-acetic acid Step 1. Concentrated sulfuric acid (30.00 mL) was cooled to −10° C. with an ice/salt bath. To this, 1,2,3,4-tetrahydro-quinoline (10.60 g, 75.60 mmol) and a solution of nitric acid (99.5%, 4.80 g, 75.60 mmol) in sulfuric acid (15.00 mL) were added simultaneously within 1 hour, so that the temperature of the reaction mixture does not exceed 10° C. The mixture was stirred then for 2.5 hours at −5° C., then poured over ice and treated with sodium carbonate (0.10 kg) until pH 8-9 was reached. The solid was filtered, washing with water, then dissolved in dichloromethane. The organic phase was washed with water, dried over magnesium sulphate and evaporated. 7-Nitro-1,2,3,4-tetrahydro-quinoline was obtained as a viscous brown oil, 13.70 g (85%), 84% purity.

Step 2. A solution of 5-chloro-2-methoxybenzenesulfonyl chloride (2.75 g, 11.20 mmol) in dichloromethane (0.15 L) was treated with pyridine (14.59 mL, 181.26 mmol) and a solution of 7-nitro-1,2,3,4-tetrahydro-quinoline (1.90 g, 10.66 mmol) in dichloromethane (6.00 mL). The mixture was stirred at room temperature for 120 hours, then the volatiles were evaporated. The residue was redissolved in dichloromethane and washed with water. The organic phase was dried over magnesium sulphate and evaporated. The residue was purified by flash chromatography (dichloromethane/methanol gradient) to yield 1-(5-chloro-2-methoxy-benzenesulfonyl)-7-nitro-1,2,3,4-tetrahydro-quinoline as an orange solid, 3.46 g (85%), MS (ISP): m/e=383.1 (M+H).

Step 3. A 27% solution of ammonium chloride in water (35.00 mL) was mixed with 1,2-dimethoxyethane (21.00 mL) and the mixture cooled to 15° C. 1-(5-Chloro-2-methoxy-benzenesulfonyl)-7-nitro-1,2,3,4-tetrahydro-quinoline (1.00 g, 26.10 mmol) was added under vigorous stirring, followed by zinc powder (2.22 g, 33.96 mmol). The mixture was warmed to room temperature and stirred for 1 hour. After filtering off the solids, the organic solvent was evaporated and the residual slurry extracted several times with ethyl acetate. The combined organic phases were dried over magnesium sulphate and evaporated. The residue was purified by flash chromatography (dichloromethane/methanol gradient) to yield 1-(5-chloro-2-methoxy-benzenesulfonyl)-1,2,3,4-tetrahydro-quinolin-7-ylamine as a brown solid, 0.32 g (35%), MS (ISP): m/e=353.2 (M+H).

Step 4. 4-Methoxycarbonylmethyl-benzoic acid (52.00 mg, 0.27 mmol) was suspended in dichloromethane (2.00 mL) and treated with thionyl chloride (95.57 mg, 0.80 mmol). The mixture was stirred at 50° C. for 18 hours, and the volatiles were evaporated. The residue was redissolved in tetrahydrofuran (2.00 mL) and treated with 1-(5-chloro-2-methoxy-benzenesulfonyl)-1,2,3,4-tetrahydro-quinolin-7-ylamine (94.48 mg, 0.27 mmol) and 4-dimethylaminopyridine (66.76 mg, 0.54 mmol). The mixture was warmed to 75° C. and stirred for 2.5 hours. The mixture was treated with HCl 1 N and the slurry extracted several times with ethyl acetate. The combined organic phases were dried over magnesium sulphate and evaporated. The residue was purified by flash chromatography (dichloromethane/methanol gradient) to yield {4-[1-(5-chloro-2-methoxy-benzenesulfonyl)-1,2,3,4-tetrahydro-quinolin-7-ylcarbamoyl]-phenyl}-acetic acid methyl ester as an off-white solid, 134.20 mg (95%), MS (ISP): m/e=529.3 (M+H).

Step 5. {4-[1-(5-Chloro-2-methoxy-benzenesulfonyl)-1,2,3,4-tetrahydro-quinolin-7-ylcarbamoyl]-phenyl}-acetic acid methyl ester (121.00 mg, 0.23 mmol) was dissolved in methanol/tetrahydrofuran 1:1 (1.40 mL) and treated at room temperature with a 1N solution of LiOH in water (0.70 mL, 0.70 mmol). The mixture was stirred at room temperature for 4 hours, then the organic solvents were evaporated and the residual aqueous phase acidified with HCl 1N (0.70 mL). The precipitated solid was filtered washing with ether, then purified by flash chromatography (dichloromethane/methanol gradient) to yield {4-[1-(5-chloro-2-methoxy-benzenesulfonyl)-1,2,3,4-tetrahydro-quinolin-7-ylcarbamoyl]-phenyl}-acetic acid as an off-white solid, 69.00 mg (59%), MS (ISP): m/e=513.5 (M−H).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |

-continued

| | |
|---|---|
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

Unless stated to the contrary, all compounds in the examples were prepared and characterized as described. All ranges recited herein encompass all combinations and sub-combinations included within that range limit. All patents and publications cited herein are hereby incorporated by reference in their entirety.

The invention claimed is:
1. A compound of formula (I):

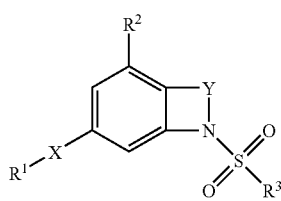

(I)

or a pharmaceutically acceptable salt or ester thereof, wherein:

X is —NHC(O)— or —C(O)NH—;
Y is —C($R^4R^5$)C($R^6R^7$)— or —C$R^4$=C$R^6$—;
$R^1$ is aryl or heteroaryl, which aryl or heteroaryl is substituted with —C($R^{12}R^{13}$)[C($R^{14}R^{15}$)]$_n$C(O)O$R^{16}$, and which aryl or heteroaryl in addition is optionally substituted with 1 to 2 substituents independently selected from the group consisting of lower-alkyl, hydroxy, halogen, lower-alkoxy, fluoro-lower-alkyl and fluoro-lower-alkoxy;

$R^2$ is hydrogen, lower-alkyl, hydroxy, halogen, lower-alkoxy, fluoro-lower-alkyl, or fluoro-lower-alkoxy;

$R^3$ is aryl which is optionally substituted with 1 to 3 substituents independently selected from the group consisting of halogen, cyano, hydroxy, lower-alkyl, fluoro-lower-alkyl, lower-alkoxy, fluoro-lower-alkoxy, lower-alkyl-C(O), lower-alkyl-C(O)—NH, lower-alkyl-C(O)—N(lower-alkyl), lower-alkyl-S(O)$_2$, NH$_2$—S(O)$_2$, N(H,lower-alkyl)-S(O)$_2$, N(lower-alkyl)$_2$-S(O)$_2$, NH$_2$—C(O), N(H,lower-alkyl)-C(O), N(lower-alkyl)$_2$-C(O) and lower-alkoxy-C(O), wherein lower-alkyl is optionally substituted with hydroxy, lower-alkoxy, NH$_2$, N(H,lower-alkyl), or N(lower-alkyl)$_2$;

$R^4$, $R^5$, $R^6$, $R^7$, $R^8$, $R^9$, $R^{10}$ and $R^{11}$ independently from each other are selected from the group consisting of hydrogen, halogen, lower-alkyl, lower-alkoxy, fluoro-lower-alkyl, fluoro-lower-alkoxy, hydroxyl, and hydroxy-lower-alkyl;

$R^{12}$, $R^{13}$, $R^{14}$ and $R^{15}$ independently from each other are selected from the group consisting of hydrogen, halogen, lower-alkyl, lower-alkoxy, fluoro-lower-alkyl, fluoro-lower-alkoxy, hydroxy, and hydroxy-lower-alkyl; or alternatively $R^{13}$ is H and $R^{12}$ is —(CH$_2$)$_{1-3}$— and forms a bridge to the aryl or heteroaryl, to which the —C($R^{12}R^{13}$)[C($R^{14}R^{15}$)]$_n$C(O)O$R^{16}$ is bound;

$R^{16}$ is hydrogen or lower-alkyl; and
n is 0 or 1.

2. A compound according to claim 1, wherein X is —NH—C(O)—.

3. A compound according to claim 1, wherein Y is —C($R^4R^5$)C($R^6R^7$)— and $R^4$, $R^5$, $R^6$, and $R^7$ are as defined in claim 1.

4. A compound according claim 1, wherein Y is C$R^4$=C$R^6$— and $R^4$, $R^5$, $R^6$, and $R^7$ are as defined in claim 1.

5. A compound according to claim 1, wherein $R^1$ is aryl or a heteroaryl selected from the group consisting of thiazolyl, pyrazolyl and thiadiazolyl, which aryl or heteroaryl is substituted with —C($R^{12}R^{13}$)[C($R^{14}R^{15}$)]$_n$C(O)O$R^{16}$, and which aryl or heteroaryl in addition is optionally substituted with lower-alkyl, wherein $R^{12}$, $R^{13}$, $R^{14}$, $R^{15}$, $R^{16}$ and n are as defined in claim 1.

6. A compound according to claim 1, wherein $R^1$ is phenyl or a heteroaryl selected from the group consisting of thiazolyl and pyrazolyl, which aryl or heteroaryl is substituted with —C($R^{12}R^{13}$)[C($R^{14}R^{15}$)]$_n$C(O)O$R^{16}$, wherein $R^{12}$, $R^{13}$, $R^{14}$, $R^{15}$, $R^{16}$ and n are as defined in claim 1.

7. A compound according to claim 1, wherein $R^1$ is 4-carboxymethyl-phenyl, 4-carboxymethyl-thiazol-2-yl, or 1-carboxymethyl-pyrazol-3-yl.

8. A compound according to claim 1, wherein $R^2$ is hydrogen or lower-alkyl.

9. A compound according to claim 1, wherein $R^2$ is hydrogen or methyl.

10. A compound according to claim 1, wherein $R^3$ is aryl which is optionally substituted with 1 to 3 substituents independently selected from the group consisting of halogen, lower-alkyl and lower-alkoxy.

11. A compound according to claim 1, wherein $R^3$ is 3,5-dimethyl-phenyl, 3-chloro-phenyl, 2-methoxy-5-chloro-phenyl, or 2-methoxy-5-methyl-phenyl.

12. A compound according to claim 1, wherein $R^4$, $R^5$, $R^6$, $R^7$, $R^8$, $R^9$, $R^{10}$ and $R^{11}$ are hydrogen.

13. A compound according to claim 1, wherein $R^{12}$, $R^{13}$, $R^{14}$ and $R^{15}$ independently from each other are hydrogen, lower-alkyl or hydroxy; or $R^{13}$ is H and $R^{12}$ is —$(CH_2)_{2-3}$— and forms a bridge to the aryl or heteroaryl to which the —$C(R^{12}R^{13})[C(R^{14}R^{15})]_nC(O)OR^{16}$ is bound.

14. A compound according to claim 1, wherein $R^{12}$-$R^{16}$ is hydrogen.

15. A compound according claim 1, wherein n is 0.

16. A compound according to claim 1, selected from the group consisting of:
- (4-{[1-(5-Chloro-2-methoxy-benzenesulfonyl)-1H-indole-6-carbonyl]-amino}-phenyl)-acetic acid,
- (4-{[1-(2-Methoxy-5-methyl-benzenesulfonyl)-1H-indole-6-carbonyl]-amino}-phenyl)-acetic acid,
- (4-{[1-(3,5-Dimethyl-benzenesulfonyl)-1H-indole-6-carbonyl]-amino}-phenyl)-acetic acid,
- (4-{[1-(3-Chloro-benzenesulfonyl)-1H-indole-6-carbonyl]-amino}-phenyl)-acetic acid,
- (4-{[1-(2-Methoxy-5-methyl-benzenesulfonyl)-2,3-dihydro-1H-indole-6-carbonyl]-amino}-phenyl)-acetic acid,
- (4-{[1-(3,5-Dimethyl-benzenesulfonyl)-2,3-dihydro-1H-indole-6-carbonyl]-amino}-phenyl)-acetic acid,
- (4-{[1-(3-Chloro-benzenesulfonyl)-2,3-dihydro-1H-indole-6-carbonyl]-amino}-phenyl)-acetic acid,
- (2-{[1-(3,5-Dimethyl-benzenesulfonyl)-2,3-dihydro-1H-indole-6-carbonyl]-amino}-thiazol-4-yl)-acetic acid, and any pharmaceutically acceptable salt or ester thereof.

17. A compound according to claim 1, selected from the group consisting of:
- (2-{[1-(3-Chloro-benzenesulfonyl)-2,3-dihydro-1H-indole-6-carbonyl]-amino}-thiazol-4-yl)-acetic acid,
- (4-{[1-(5-Chloro-2-methoxy-benzenesulfonyl)-2,3-dihydro-1H-indole-6-carbonyl]-amino}-phenyl)-acetic acid,
- (2-{[1-(5-Chloro-2-methoxy-benzenesulfonyl)-2,3-dihydro-1H-indole-6-carbonyl]-amino}-thiazol-4-yl)-acetic acid,
- (2-{[1-(5-Chloro-2-methoxy-benzenesulfonyl)-2,3-dihydro-1H-indole-6-carbonyl]-amino}-5-methyl-thiazol-4-yl)-acetic acid,
- (3-{[1-(5-Chloro-2-methoxy-benzenesulfonyl)-2,3-dihydro-1H-indole-6-carbonyl]-amino}-pyrazol-1-yl)-acetic acid,
- (4-{[1-(5-Chloro-2-methoxy-benzenesulfonyl)-4-methyl-2,3-dihydro-1H-indole-6-carbonyl]-amino}-phenyl)-acetic acid,
- (2-{[1-(5-Chloro-2-methoxy-benzenesulfonyl)-4-methyl-2,3-dihydro-1H-indole-6-carbonyl]-amino}-thiazol-4-yl)-acetic acid, and any pharmaceutically acceptable salt or ester thereof.

18. A compound according to claim 1, selected from the group consisting of:
- (2-{[1-(3,5-Dimethyl-benzenesulfonyl)-2,3-dihydro-1H-indole-6-carbonyl]-amino}-thiazol-4-yl)-acetic acid,
- (2-{[1-(3-Chloro-benzenesulfonyl)-2,3-dihydro-1H-indole-6-carbonyl]-amino}-thiazol-4-yl)-acetic acid,
- (4-{[1-(5-Chloro-2-methoxy-benzenesulfonyl)-2,3-dihydro-1H-indole-6-carbonyl]-amino}-phenyl)-acetic acid,
- (2-{[1-(5-Chloro-2-methoxy-benzenesulfonyl)-2,3-dihydro-1H-indole-6-carbonyl]-amino}-thiazol-4-yl)-acetic acid,
- (3-{[1-(5-Chloro-2-methoxy-benzenesulfonyl)-2,3-dihydro-1H-indole-6-carbonyl]-amino}-pyrazol-1-yl)-acetic acid,
- (4-{[1-(5-Chloro-2-methoxy-benzenesulfonyl)-4-methyl-2,3-dihydro-1H-indole-6-carbonyl]-amino}-phenyl)-acetic acid,
- (2-{[1-(5-Chloro-2-methoxy-benzenesulfonyl)-4-methyl-2,3-dihydro-1H-indole-6-carbonyl]-amino}-thiazol-4-yl)-acetic acid, and any pharmaceutically acceptable salt or ester thereof.

19. A pharmaceutical composition comprising a therapeutically effective amount of a compound of claim 1 and a pharmaceutically acceptable carrier.

\* \* \* \* \*